(12) United States Patent
Yamazaki et al.

(10) Patent No.: US 12,099,587 B2
(45) Date of Patent: Sep. 24, 2024

(54) COMPOSITE DEVICE AND PROGRAM

(71) Applicant: SEMICONDUCTOR ENERGY LABORATORY CO., LTD., Atsugi (JP)

(72) Inventors: Shunpei Yamazaki, Tokyo (JP); Koji Kusunoki, Kanagawa (JP); Daisuke Kubota, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 268 days.

(21) Appl. No.: 17/627,422

(22) PCT Filed: Jul. 13, 2020

(86) PCT No.: PCT/IB2020/056542
§ 371 (c)(1),
(2) Date: Jan. 14, 2022

(87) PCT Pub. No.: WO2021/019335
PCT Pub. Date: Feb. 4, 2021

(65) Prior Publication Data
US 2022/0253517 A1    Aug. 11, 2022

(30) Foreign Application Priority Data

Jul. 26, 2019  (JP) .................. 2019-138151

(51) Int. Cl.
*G06F 21/32*  (2013.01)
*G06V 40/12*  (2022.01)
*G06V 40/13*  (2022.01)

(52) U.S. Cl.
CPC .............. *G06F 21/32* (2013.01); *G06V 40/13* (2022.01); *G06V 40/1365* (2022.01)

(58) Field of Classification Search
CPC .......... G06F 21/30; G06F 21/31; G06F 21/32; G06V 40/1365; G06V 40/1376; G06V 40/13
See application file for complete search history.

(56) References Cited

U.S. PATENT DOCUMENTS 7,751,600 B2    7/2010  Yamazaki et al.
8,077,934 B2 *  12/2011 Fenrich ............. G06V 40/1324
                                                      382/126
(Continued)

FOREIGN PATENT DOCUMENTS

CN    107005845 A    8/2017
CN    109475328 A    3/2019
(Continued)

OTHER PUBLICATIONS

International Search Report (Application No. PCT/IB2020/056542) Dated Oct. 20, 2020.
(Continued)

*Primary Examiner* — Hosuk Song
(74) *Attorney, Agent, or Firm* — Fish & Richardson P.C.

(57) ABSTRACT

A composite device with a high security level is provided. A composite device capable of inhibiting unauthorized use favorably is provided. The composite device includes a control portion, a detection portion, an authentication portion, and a memory portion. The detection portion has a function of detecting a touch and a function of obtaining first fingerprint data of a finger touching the detection portion. The authentication portion has a function of executing user authentication processing. The memory portion has a function of retaining second fingerprint data registered in advance. The control portion has a function of bringing a system into an unlocked state when the authentication portion authenticates a user and a function of comparing the first fingerprint data obtained by the detection portion and (Continued)

the second fingerprint data when the detection portion detects a touch, and bringing the system into a locked state in the case where those data do not match.

5 Claims, 19 Drawing Sheets

(56) References Cited

U.S. PATENT DOCUMENTS

| | | | |
|---|---|---|---|
| 9,077,523 B2 | 7/2015 | Tadokoro | |
| 10,216,975 B1 * | 2/2019 | He | G06V 10/143 |
| 10,318,791 B2 * | 6/2019 | He | G06V 40/1306 |
| 10,410,037 B2 * | 9/2019 | He | G06F 3/0412 |
| 10,956,706 B2 * | 3/2021 | Wang | G06F 3/0488 |
| 11,487,373 B2 * | 11/2022 | Kubota | G06V 40/1318 |
| 11,797,139 B2 * | 10/2023 | Van Ostrand | G06V 40/1306 |
| 11,804,064 B2 * | 10/2023 | Kusunoki | G06V 40/1365 |
| 2009/0079345 A1 | 3/2009 | Inuiya | |
| 2014/0056493 A1 | 2/2014 | Gozzini | |
| 2016/0205094 A1 | 7/2016 | Harthattu et al. | |
| 2017/0337413 A1 | 11/2017 | Bhat et al. | |
| 2021/0202549 A1 | 7/2021 | Yoneda et al. | |
| 2021/0279449 A1 | 9/2021 | Yamazaki et al. | |
| 2021/0327979 A1 | 10/2021 | Kamada et al. | |
| 2022/0029121 A1 | 1/2022 | Yamazaki et al. | |

FOREIGN PATENT DOCUMENTS

| | | |
|---|---|---|
| EP | 3243338 A | 11/2017 |
| JP | 2007-081203 A | 3/2007 |
| JP | 2009-081297 A | 4/2009 |
| JP | 2010-093635 A | 4/2010 |
| JP | 2012-168768 A | 9/2012 |
| JP | 2018-507461 | 3/2018 |
| JP | 2019-525290 | 9/2019 |
| KR | 2017-0104454 A | 9/2017 |
| KR | 2019-0028429 A | 3/2019 |
| WO | WO-2016/111808 | 7/2016 |
| WO | WO-2017/214582 | 12/2017 |

OTHER PUBLICATIONS

Written Opinion (Application No. PCT/IB2020/056542) Dated Oct. 20, 2020.

* cited by examiner

COMPOSITE DEVICE AND PROGRAM

CROSS REFERENCE TO RELATED APPLICATIONS

This application is a U.S. National Phase Application under 35 U.S.C. § 371 of International Application PCT/IB2020/056542, filed on Jul. 13, 2020, which is incorporated by reference and claims the benefit of a foreign priority application filed in Japan on Jul. 26, 2019, as Application No. 2019-138151.

TECHNICAL FIELD

One embodiment of the present invention relates to an electronic device. One embodiment of the present invention relates to an authentication method. One embodiment of the present invention relates to a display device. One embodiment of the present invention relates to a program.

Note that one embodiment of the present invention is not limited to the above technical field. Examples of the technical field of one embodiment of the present invention disclosed in this specification and the like include a semiconductor device, a display device, a light-emitting device, a power storage device, a memory device, an electronic device, a lighting device, an input device, an input/output device, a driving method thereof, and a manufacturing method thereof. A semiconductor device generally means a device that can function by utilizing semiconductor characteristics.

BACKGROUND ART

In recent years, information terminal devices, for example, mobile phones such as smartphones, tablet information terminals, and laptop PCs (personal computers) have been widely used. Such information terminal devices often include personal information or the like, and thus various authentication technologies for preventing abuse have been developed.

For example, Patent Document 1 discloses an electronic device including a fingerprint sensor in a push button switch portion.

REFERENCE

Patent Document

[Patent Document 1] United States Published Patent Application No. 2014/0056493

SUMMARY OF THE INVENTION

Problems to be Solved by the Invention

An object of one embodiment of the present invention is to provide a composite device with a high security level. Another object is to provide a composite device capable of inhibiting unauthorized use favorably. Another object is to provide a novel composite device.

Note that the description of these objects does not preclude the existence of other objects. One embodiment of the present invention does not have to achieve all these objects. Objects other than these can be derived from the description of the specification, the drawings, the claims, and the like.

Means for Solving the Problems

One embodiment of the present invention is a composite device including a control portion, a detection portion, an authentication portion, and a memory portion. The detection portion has a function of detecting a touch and a function of obtaining first fingerprint data of a finger touching the detection portion. The authentication portion has a function of executing user authentication processing. The memory portion has a function of retaining second fingerprint data registered in advance. The control portion has a function of bringing a system into an unlocked state when the authentication portion authenticates a user, and a function of comparing the first fingerprint data obtained by the detection portion and the second fingerprint data when the detection portion detects a touch, and bringing the system into a locked state in the case where those data do not match.

One embodiment of the present invention is a composite device including a control portion, a display portion, an authentication portion, and a memory portion. The display portion has a function of displaying an image on a screen, a function of detecting a touch on the screen, and a function of obtaining first fingerprint data of a finger touching the screen. The authentication portion has a function of executing user authentication processing. The memory portion has a function of retaining second fingerprint data registered in advance. The control portion has a function of bringing a system into an unlocked state when the authentication portion authenticates a user, and a function of comparing the first fingerprint data obtained by the display portion and the second fingerprint data when the display portion detects a touch, and bringing the system into a locked state in the case where those data do not match.

In the above, the display portion preferably includes a plurality of pixels. In that case, it is preferable that the pixel include a light-emitting element and a light-receiving element, and the light-emitting element and the light-receiving element be provided on the same plane.

In the above, the light-emitting element preferably has a stacked-layer structure in which a first electrode, a light-emitting layer, and a common electrode are stacked. The light-receiving element preferably has a stacked-layer structure in which a second electrode, an active layer, and the common electrode are stacked. In that case, the light-emitting layer and the active layer preferably contain different organic compounds from each other. Furthermore, it is preferable that the first electrode and the second electrode be provided on the same plane to be apart from each other and the common electrode be provided to cover the light-emitting layer and the active layer.

Alternatively, in the above, the light-emitting element preferably has a stacked-layer structure in which a first electrode, a common layer, a light-emitting layer, and a common electrode are stacked. The light-receiving element preferably has a stacked-layer structure in which a second electrode, the common layer, an active layer, and the common electrode are stacked. In that case, the light-emitting layer and the active layer preferably contain different organic compounds from each other. Furthermore, it is preferable that the first electrode and the second electrode be provided on the same plane to be apart from each other, the common electrode be provided to cover the light-emitting layer and the active layer, and the common layer be provided to cover the first electrode and the second electrode.

In the above, it is preferable that the light-emitting element have a function of emitting visible light, and the light-receiving element have a function of receiving the visible light emitted from the light-emitting element.

Alternatively, in the above, it is preferable that the light-emitting element have a function of emitting infrared light, and the light-receiving element have a function of receiving the infrared light emitted from the light-emitting element.

Another embodiment of the present invention is a program that is executed by a composite device including a control portion, a detection portion, and an authentication portion. Here, the detection portion has a function of detecting a touch and a function of obtaining first fingerprint data of a finger touching the detection portion. The program of one embodiment of the present invention includes the following steps: a step of bringing a system into an unlocked state in the case where the authentication portion executes user authentication and authenticates a user, a step of obtaining the first fingerprint data when the detection portion detects a touch, a step in which the control portion compares the first fingerprint data and second fingerprint data that is registered in advance, a step in which the control portion executes processing in accordance with the touch in the case where the first fingerprint data and the second fingerprint data match, and a step in which the control portion brings the system into a locked state in the case where the first fingerprint data and the second fingerprint data do not match.

Effect of the Invention

According to one embodiment of the present invention, a composite device with a high security level can be provided. A composite device capable of inhibiting unauthorized use favorably can be provided. Alternatively, a novel composite device can be provided.

Note that the description of these effects does not preclude the existence of other effects. One embodiment of the present invention does not have to have all of these effects. Effects other than these can be derived from the description of the specification, the drawings, the claims, and the like.

MODE FOR CARRYING OUT THE INVENTION

Figure 1:
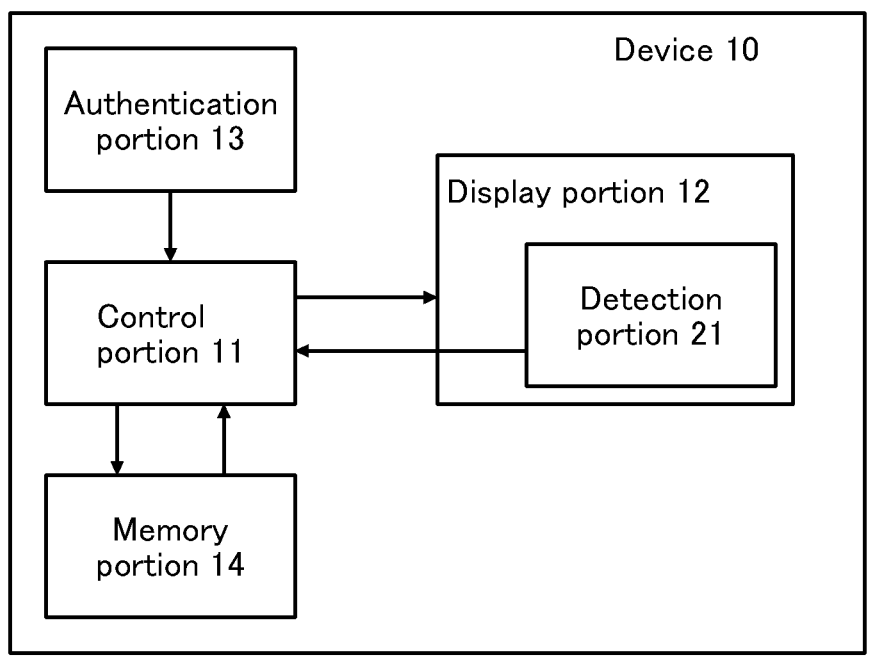
FIG. 1 is a diagram illustrating a structure example of a device.

Hereinafter, embodiments are described with reference to the drawings. Note that the embodiments can be implemented in many different modes, and it is readily understood by those skilled in the art that modes and details thereof can be changed in various ways without departing from the spirit and scope thereof. Thus, the present invention should not be construed as being limited to the following description of the embodiments.

Note that in structures of the invention described below, the same portions or portions having similar functions are denoted by the same reference numerals in different drawings, and a description thereof is not repeated. Furthermore, the same hatch pattern is used for the portions having similar functions, and the portions are not especially denoted by reference numerals in some cases.

Note that in each drawing described in this specification, the size, the layer thickness, or the region of each component is exaggerated for clarity in some cases. Therefore, they are not limited to the illustrated scale.

Note that in this specification and the like, the ordinal numbers such as "first" and "second" are used in order to avoid confusion among components and do not limit the number.

Embodiment 1

In this embodiment, a composite device of one embodiment of the present invention and a performance method of the composite device is described.

Note that in the drawings attached to this specification, the block diagram in which components are classified according to their functions and shown as independent blocks is illustrated; however, it is difficult to separate actual components completely according to their functions, and one component may be related to a plurality of functions or a plurality of components may achieve one function.

The composite device of one embodiment of the present invention has a function of obtaining a fingerprint of a finger touching an input means such as a screen (also referred to as a touch panel) or a touch pad and executing user authentication processing using the fingerprint. Every time a user touches the screen or touch pad to operate the device, the authentication processing can be executed; thus, a device with an extremely high security level can be achieved.

Meanwhile, in the case of a device using only an authentication method using a password or the like, for example, there is a risk of unauthorized use of the device by a malicious user obtaining the password improperly. Furthermore, even in the case of using only biometric authentication such as fingerprint authentication or face authentication, there is a problem in that the device can be unlocked while an authentic user is unaware, for example, sleeping.

In the composite device of one embodiment of the present invention, authentication processing is executed every time the composite device is operated using a screen or touch pad; thus, even in the case where unlocking the device or logging in to various systems is performed by an unauthorized method, the device can immediately turn into a locked state to prevent a malicious user from using the device.

A more specific structure example of the composite device of one embodiment of the present invention is described below with reference to drawings.

[Structure Example of Composite Device]

FIG. 1 illustrates a block diagram of a device 10 of one embodiment of the present invention. The device 10 includes a control portion 11, a display portion 12, an authentication portion 13, and a memory portion 14. The display portion 12 includes a detection portion 21. The device 10 can be used as an electronic device such as an information terminal device, for example.

The authentication portion 13 has a function of executing user authentication processing. The authentication portion 13 can execute the user authentication processing and then output the result to the control portion 11.

Examples of authentication methods that can be applied to the authentication portion 13 include authentication methods employing user input such as password entry or pattern entry, authentication methods employing user's biological information (also referred to as biometric authentication) such as fingerprint authentication, vein authentication, voiceprint authentication, face authentication, and iris authentication, and the like.

The display portion 12 has a function of displaying an image, a function of detecting a touch, and a function of obtaining fingerprint data of a finger touching a screen or the like. Here, an example where the display portion 12 includes the detection portion 21 is illustrated. The detection portion 21 is a portion having, out of the above functions of the display portion 12, the function of detecting a touch and the function of obtaining fingerprint data. The display portion 12 can also be referred to as a touch panel with a fingerprint data obtaining function.

The detection portion 21 has a function of outputting the position information of a finger touching a screen to the control portion 11. Furthermore, the detection portion 21 has a function of capturing a fingerprint image of a finger touching the screen and outputting the image data as fingerprint data to the control portion 11.

It is preferable that the display portion 12 be capable of obtaining fingerprint data of a finger touching any position on the screen. In other words, a range where the touch sensor functions and a range where fingerprint data can be obtained preferably match or substantially match on the screen.

The memory portion 14 has a function of retaining user's fingerprint data registered in advance. The memory portion 14 can output the fingerprint data to the control portion 11 in accordance with the request from the control portion 11.

The memory portion 14 preferably retains fingerprint data of all the fingers of a user operating the screen. For example, two kinds of fingerprint data of user's right and left index fingers can be retained. In addition to them, it is preferable that one or more kinds of fingerprint data of a middle finger, a ring finger, a little finger, and a thumb be retained.

The control portion 11 has a function of bringing the system from the locked state into the unlocked state in the case where a user is authenticated by user authentication executed by the authentication portion 13.

Furthermore, the control portion 11 has a function of requesting the detection portion 21 to obtain fingerprint data when a touch is detected by the detection portion 21. Then, the control portion 11 has a function of comparing the fingerprint data input from the detection portion 21 with the fingerprint data registered in advance. When the control portion 11 determines that these two kinds of data match, the control portion 11 executes processing in accordance with touch operation by a user. On the other hand, when the control portion 11 determines that the two kinds of data do not match, the control portion 11 brings the system from the unlocked state into the locked state.

Examples of a fingerprint authentication method executed by the control portion 11 include a method using the degree of similarity between two images compared, e.g., a template matching method or a pattern matching method. Alternatively, fingerprint authentication processing may be executed by inference using machine learning. At this time, the fingerprint authentication processing is preferably executed by inference using a neural network, in particular.

The control portion 11 can function as, for example, a central processing unit (CPU). The control portion 11 interprets and executes instructions from various programs with use of a processor to process various kinds of data and control programs. Programs that might be executed by the processor may be stored in a memory region of the processor or may be stored in the memory portion 14.

[Operation Example of Device 10]

Figure 2:
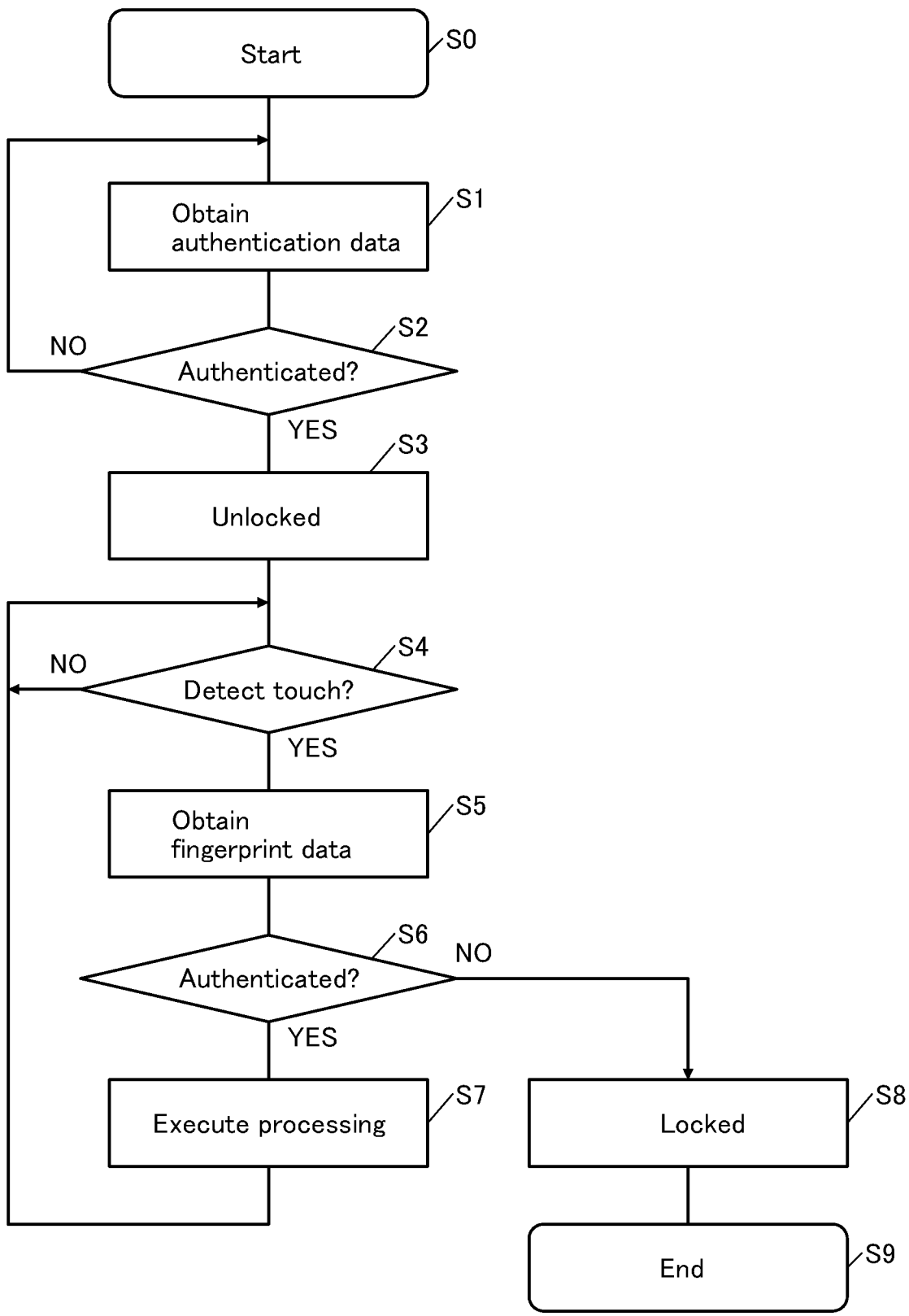
FIG. 2 is a diagram showing a performance method of a device.

An operation example of the device 10 is described below. FIG. 2 is a flow chart of the operation of the device 10. The flow chart shown in FIG. 2 includes Step S0 to Step S9.

First, the operation starts in Step S0. The operation starts when power-on of an electronic device incorporating the device 10, a press of a physical button, a touch on a display portion 12 by a user, a large change in the attitude of the electronic device, or the like is sensed, for example. At this time, the device 10 is in the locked state (also referred to as a log-out state or log-off state).

In Step S1, authentication data that is necessary for the authentication processing of the authentication portion 13 is obtained.

In Step S2, the authentication portion 13 executes user authentication processing on the basis of the authentication data. When the user is authenticated, the processing proceeds to Step S3. When the user is not authenticated, the processing returns to Step S1 while the system remains in the locked state.

In Step S3, the control portion 11 brings the system into the unlocked state (also referred to as bringing the system into a log-in state).

In Step S4, the detection portion 21 detects touch operation. When a touch is detected, the processing proceeds to Step S5. When touch operation is not performed, the system is in standby until touch operation is performed while remaining in the unlocked state (the processing proceeds to Step S4 again).

In the case where touch operation is not performed for a certain period in Step S4, the control portion 11 may bring the system into the locked state. At this time, the processing may proceed to Step S1.

In Step S5, the detection portion 21 obtains fingerprint data. The detection portion 21 outputs the obtained fingerprint data to the control portion 11.

In Step S6, the control portion 11 executes fingerprint authentication processing. Specifically, the fingerprint data retained in the memory portion 14 and the fingerprint data obtained by the detection portion 21 are compared and determined whether the data match or not. When the data is authenticated (when the two kinds of fingerprint data are determined to match), the processing proceeds to Step S7. On the other hand, when the data is not authenticated (when the two kinds of fingerprint data are not determined to match), the processing proceeds to Step S8.

In Step S7, the control portion 11 executes processing on the basis of the touch operation detected in Step S4. The examples of touch operation include operations such as tap, long tap, swipe, pinch in, pinch out, flick, and drag.

After processing is executed in Step S7, the processing proceeds to Step S4 and the system is in standby until touch operation is performed again.

In Step S8, the system is brought into the locked state. This renders the electronic device unavailable to the user operating the electronic device. Alternatively, available functions are limited.

In Step S9, the operation ends. In Step S9, the power may be turned off, the system may be shut down, or the processing may proceed to Step S1 again while the system remains in the locked state (or a log-out state).

The above is the description of the flow chart shown in FIG. 2.

Note that a processing method, an operation method, a performance method, a display method, or the like that is executed by the composite device of one embodiment of the present invention might be described as a program, for example. For example, a program in which the processing method, operation method, performance method, display method, or the like that is described above as an example and executed by the device 10 and the like is written can be stored in a non-temporary storage medium and can be read and executed by an arithmetic device or the like included in the control portion 11 of the device 10. Accordingly, a program that makes hardware execute the performance method or the like described above as an example and a non-temporary memory medium including the program are of embodiments of the present invention.

MODIFICATION EXAMPLE

Figure 3:
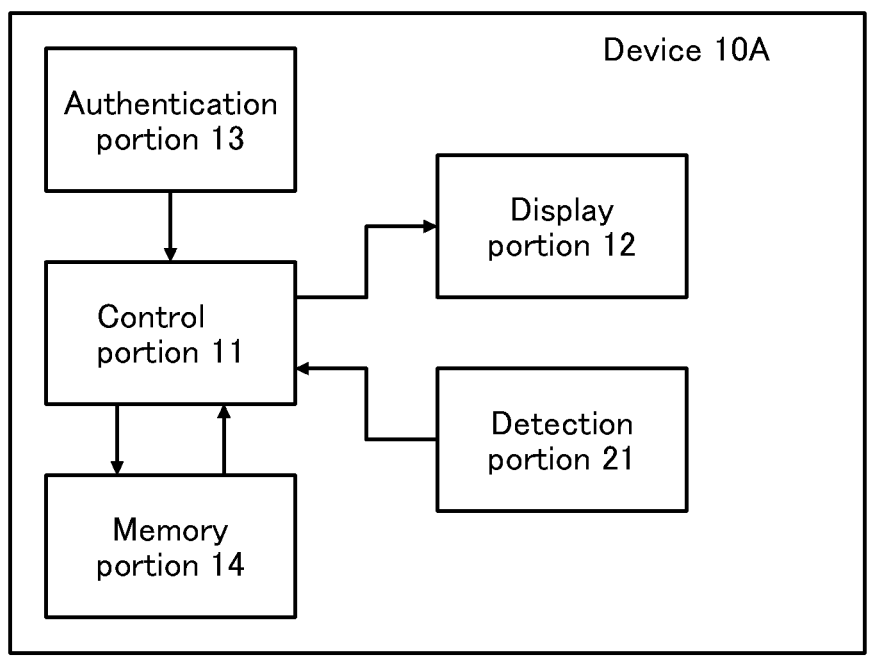
FIG. 3 is a diagram illustrating a structure example of a device.

Although the display portion 12 includes the detection portion 21 in the above example, they may be provided separately. A device 10A illustrated in FIG. 3 is an example in which the detection portion 21 is not included in the display portion 12.

Examples of the detection portion 21 of the device 10A include a touch pad that does not have an image display function.

Alternatively, the device 10A may include the following two: the display portion 12 not having a function of obtaining fingerprint data and the detection portion 21 having a function of displaying an image. In other words, a touch panel with a fingerprint data obtaining function may be used as the detection portion 12 that is an input means, and the display portion 12 may be separately included as an image display means.

Specific Example

A specific example of an electronic device to which the composite device of one embodiment of the present invention is applied is described below.

Figure 4A:
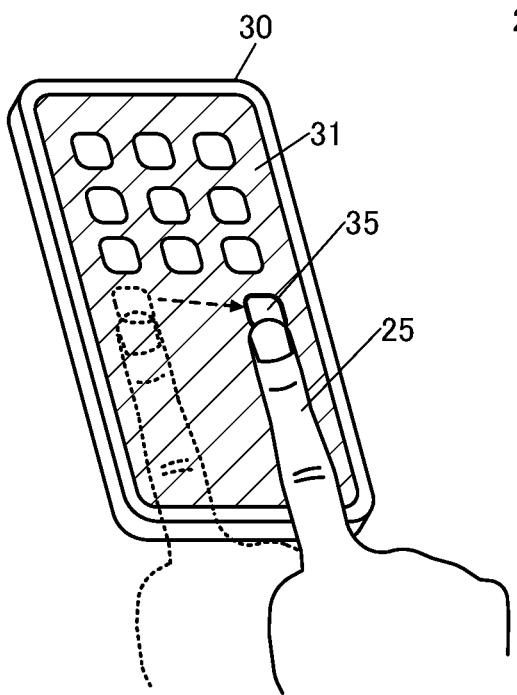
FIG. 4A to FIG. 4D are diagrams illustrating structure examples of an electronic device and examples of performance methods thereof.

FIG. 4A schematically illustrates an electronic device 30 and a finger 25 operating the electronic device. The electronic device 30 includes a display portion 31. The electronic device 30 is a portable information terminal device functioning as a smartphone, for example.

In FIG. 4A, the fingertip of the finger 25 touches the display portion 31. At this time, the display portion 31 can obtain fingerprint data 26 of the finger 25.

Figure 4B:
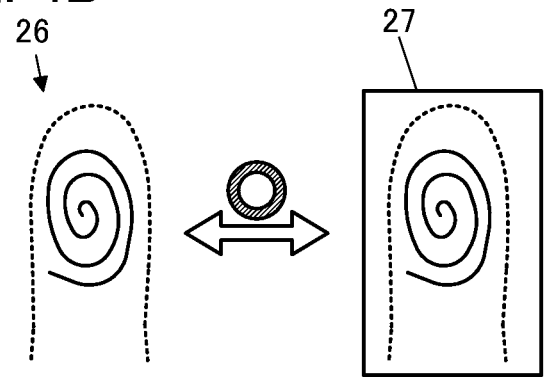

FIG. 4B illustrates the fingerprint data 26 obtained by the display portion 31 and fingerprint data 27 of a user registered in advance in the electronic device 30. In FIG. 4B, it is determined that the fingerprint data 26 and the fingerprint data 27 match. Accordingly, since the user using the electronic device 30 is authenticated, the user can move an icon image 35 by drag operation as illustrated in FIG. 4A, for example.

Figure 4C:
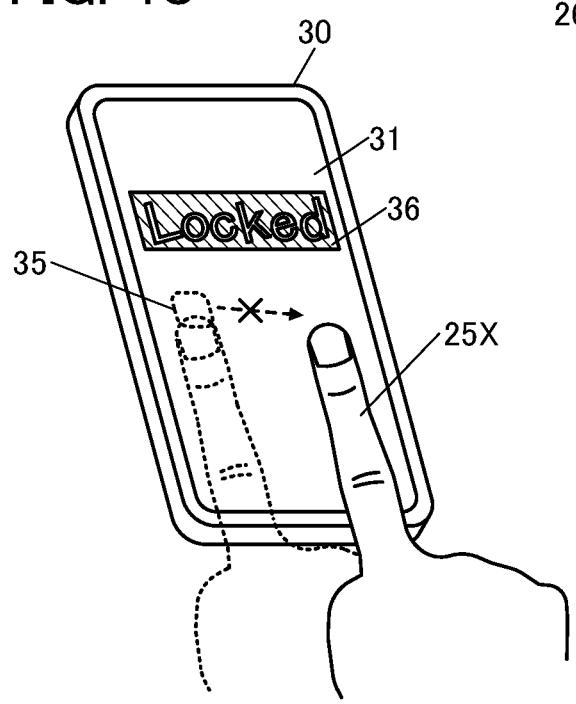
Figure 4D:
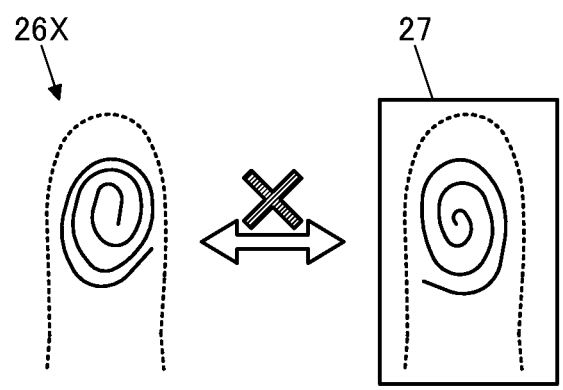

FIG. 4C illustrates a state where the electronic device 30 is to be operated with a finger 25X of a user who is not registered in the electronic device 30. As illustrated in FIG. 4D, the user is not authenticated because fingerprint data 26X of the finger 25X and the fingerprint data 27 registered in advance do not match.

In FIG. 4C, the electronic device 30 is in the locked state (or the log-out state) so as not to be used by the user. Therefore, even when the operation to move the icon image 35 with the finger 25X is performed, the electronic device 30 does not react (the operation is not accepted). At this time, as illustrated in FIG. 4C, the display portion 31 may display information 36 indicating that the electronic device 30 is in the locked state.

Figure 5A:
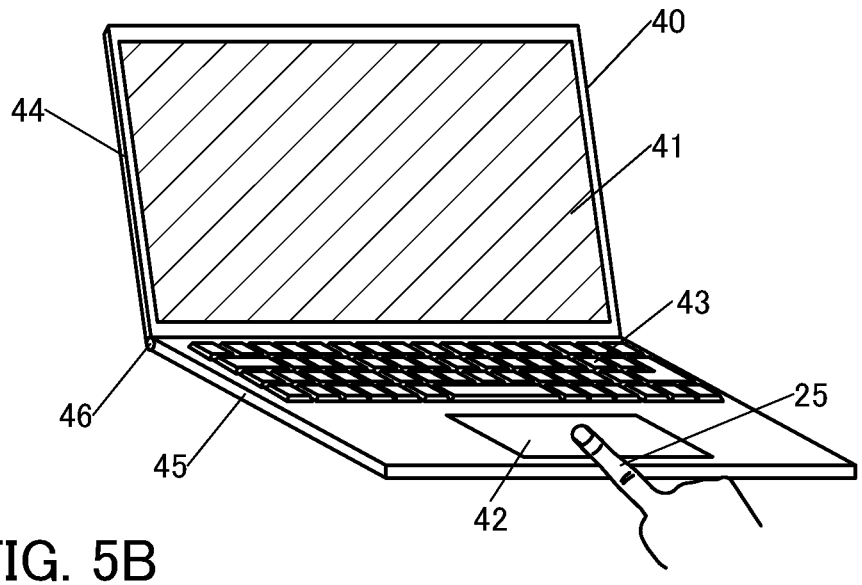
FIG. 5A to FIG. 5C are diagrams illustrating structure examples of electronic devices.

FIG. 5A illustrates an electronic device 40 to which the composite device of one embodiment of the present invention is applied. The electronic device 40 functions as a laptop personal computer.

The electronic device 40 includes a display portion 41, an input portion 42, a plurality of input keys 43, a housing 44, a housing 45, a hinge portion 46, and the like. The housing 44 is provided with the display portion 41. The housing 45 is provided with the input portion 42 and the input keys 43. The housing 44 and the housing 45 are joined together by the hinge portion 46.

The input portion 42 functions as a touch pad. The input portion 42 has a function of obtaining the information of a position where the fingertip of the finger 25 touches and the fingerprint data of the fingertip.

In the case where a touch panel is used for the display portion 41, the display portion 41 preferably has a function of obtaining fingerprint data.

Figure 5B:
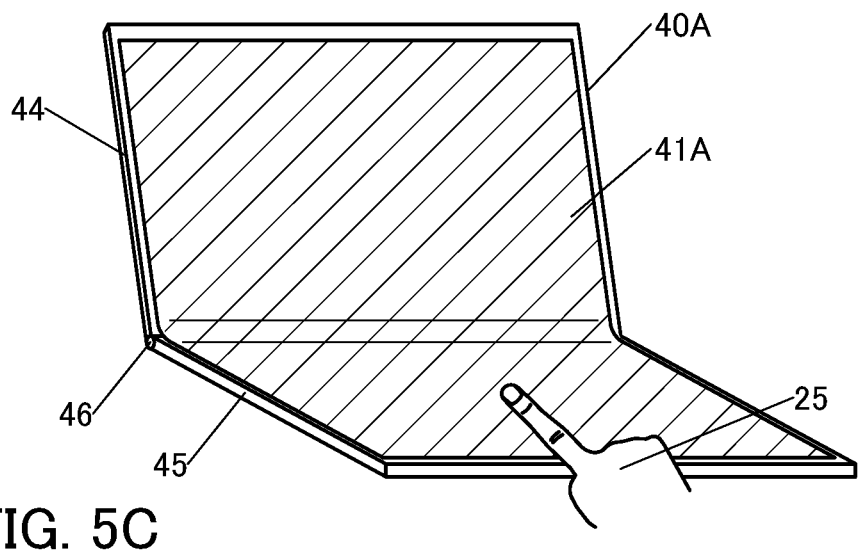

FIG. 5B illustrates an electronic device 40A using a flexible display for a display portion 41A. The display portion 41A is provided across the housing 44 and the housing 45. Thus, seamless display across two housings is possible.

The display portion 41A has a function of displaying an image, a function of obtaining the information of a position where the fingertip of the finger 25 touches, and a function of obtaining the fingerprint data of the fingertip.

Figure 5C:
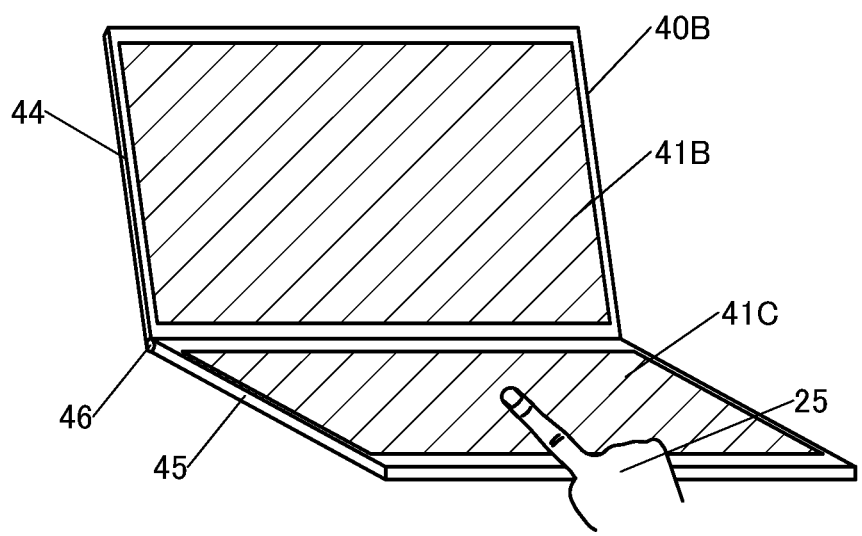

FIG. 5C illustrates an electronic device 40B provided with display portions on each of the two housings. The housing 44 is provided with a display portion 41B. The housing 45 is provided with a display portion 41C.

At least one of the display portion 41B and the display portion 41C, preferably both of them, has/have a function of displaying an image, a function of obtaining the information of a position where the fingertip of the finger 25 touches, and a function of obtaining the fingerprint data of the fingertip.

The above is the description of the specific example.

At least part of this embodiment can be implemented in combination with the other embodiments described in this specification as appropriate.

Embodiment 2

In this embodiment, a display device that can be used for the display portion of the composite device of one embodiment of the present invention is described. A display device shown below as an example includes a light-emitting element and a light-receiving element. The display device has a function of displaying an image, a function of performing position detection with reflected light from an object to be detected, and a function of capturing an image of a fingerprint or the like with reflected light from an object to be detected. The display device shown below as an example can also be regarded to have a function of a touch panel and a function of a fingerprint sensor.

A display device according to one embodiment of the present invention includes a light-emitting element emitting first light (a light-emitting device) and a light-receiving element receiving the first light (a light-receiving device). The light-receiving element is preferably a photoelectric conversion element. As the first light, visible light or infrared light can be used. In the case where infrared light is used as the first light, in addition to the light-emitting element emitting the first light, a light-emitting element emitting visible light can be included.

In addition, the display device includes a pair of substrates (also referred to as a first substrate and a second substrate). The light-emitting element and the light-receiving element are arranged between the first substrate and the second substrate. The first substrate is positioned on a display surface side, and the second substrate is positioned on a side opposite to the display surface side.

Visible light is emitted from the light-emitting element to the outside through the first substrate. A plurality of such light-emitting elements arranged in a matrix are included in the display device, so that an image can be displayed.

The first light emitted from the light-emitting element reaches a surface of the first substrate. Here, when an object touches the surface of the first substrate, the first light is scattered at an interface between the first substrate and the object, and part of the scattered light enters the light-receiving element. When receiving the first light, the light-receiving element can convert the light into an electric signal in accordance with the intensity of the first light and output the electric signal. A plurality of light-receiving elements arranged in a matrix are included in the display device, whereby positional information, shape, or the like of the object touching the first substrate can be detected. That is, the display device can function as an image sensor panel, a touch sensor panel, or the like.

Note that even in the case where the object does not touch the surface of the first substrate, the first light that has passed through the first substrate is reflected or scattered in the surface of the object, and the reflected light or the scattered light enters the light-receiving element through the first substrate. Thus, the display device can also be used as a non-contact touch sensor panel (also referred to as a near-touch panel).

In the case where visible light is used as the first light, the first light used for image display can be used as a light source of a touch sensor. In that case, the light-emitting element has a function of a display element and a function of a light source, so that the structure of the display device can be simplified. In contrast, in the case where infrared light is used as the first light, a user does not perceive the infrared light, so that image capturing or sensing can be performed by the light-receiving element without a reduction in visibility of a displayed image.

In the case where infrared light is used as the first light, infrared light, preferably near-infrared light is used. In particular, near-infrared light having one or more peaks in the range of a wavelength greater than or equal to 700 nm and less than or equal to 2500 nm can be favorably used. In particular, the use of light having one or more peaks in the range of a wavelength greater than or equal to 750 nm and less than or equal to 1000 nm is preferable because it permits an extensive choice of a material used for an active layer of the light-receiving element.

When a fingertip touches a surface of the display device, an image of the shape of a fingerprint can be captured. A fingerprint has a depression and a projection. When a finger touches a light guide plate, the first light is likely to be scattered by the projection of the fingerprint touching the surface of the first substrate. Therefore, the intensity of scattered light that enters the light-receiving element overlapping with the projection of the fingerprint is high, and the intensity of scattered light that enters the light-receiving element overlapping with the depression is low. Utilizing this, a fingerprint image can be captured. A device including the display device of one embodiment of the present invention can perform fingerprint authentication, which is a kind of biometric authentication, by utilizing a captured fingerprint image.

In addition, the display device can also capture an image of a blood vessel, especially a vein of a finger, a hand, or the like. For example, since light having a wavelength of 760 nm and its vicinity is not absorbed by reduced hemoglobin in a vein, reflected light from a palm, a finger, or the like is received by the light-receiving element and captured as an image, so that the position of the vein can be detected. The device including the display device of one embodiment of the present invention can perform vein authentication, which is a kind of biometric authentication, by utilizing a captured vein image.

In addition, the device including the display device of one embodiment of the present invention can also perform touch sensing, fingerprint authentication, and vein authentication at the same time. Thus, biometric authentication with a high security level can be executed at low cost without increasing the number of components.

The light-receiving element is preferably an element that can receive both infrared light and visible light. In that case, as the light-emitting element, both a light-emitting element emitting infrared light and a light-emitting element emitting visible light are preferably included. Accordingly, visible light is reflected by a user's finger and reflected light is received by the light-receiving element, so that an image of a fingerprint can be captured. Furthermore, an image of the shape of a vein can be captured with infrared light. Accordingly, both fingerprint authentication and vein authentication can be executed in one display device. Moreover, fingerprint image capturing and vein image capturing may be executed either at different timings or at the same time. In the case where fingerprint image capturing and vein image capturing are performed at the same time, image data including both data on the shape of a fingerprint and data on the shape of a vein can be obtained, so that biometric authentication with higher accuracy can be achieved.

The display device of one embodiment of the present invention may have a function of sensing user's health conditions. For example, by utilizing changes in reflectance and transmittance with respect to visible light and infrared light in accordance with a change in blood oxygen saturation, temporal modulation of the oxygen saturation is obtained, from which a heart rate can be measured. Furthermore, a glucose concentration in dermis, a neutral fat concentration in the blood, or the like can also be measured with infrared light or visible light. The device including the display device of one embodiment of the present invention can be used as a health care device capable of obtaining index data on user's health conditions.

As the first substrate, a sealing substrate for sealing the light-emitting element, a protective film, or the like can be used. In addition, a resin layer may be provided between the first substrate and the second substrate to attach the first substrate and the second substrate to each other.

Here, as the light-emitting element, an EL element such as an OLED (Organic Light Emitting Diode) or a QLED (Quantum-dot Light Emitting Diode) is preferably used. As a light-emitting substance included in the EL element, a substance which emits fluorescence (a fluorescent material), a substance which emits phosphorescence (a phosphorescent material), an inorganic compound (e.g., a quantum dot material), a substance which exhibits thermally activated delayed fluorescence (a thermally activated delayed fluorescent (TADF) material), and the like can be given. Alternatively, an LED such as a micro-LED (Light Emitting Diode) can be used as the light-emitting element.

As the light-receiving element, a pn photodiode or a pin photodiode can be used, for example. The light-receiving element functions as a photoelectric conversion element that detects light incident on the light-receiving element and generates charge. The amount of generated charge in the photoelectric conversion element is determined depending on the amount of incident light. It is particularly preferable to use an organic photodiode including a layer containing an organic compound as the light-receiving element. An organic photodiode, which is easily made thin, lightweight, and large in area and has a high degree of freedom for shape and design, can be used in a variety of display devices.

The light-emitting element can have a stacked-layer structure including a light-emitting layer between a pair of electrodes, for example. The light-receiving element can have a stacked-layer structure including an active layer between a pair of electrodes. A semiconductor material can be used for the active layer of the light-receiving element. For example, an inorganic semiconductor material such as silicon can be used.

An organic compound is preferably used for the active layer of the light-receiving element. In that case, one electrode of the light-emitting element and one electrode of the light-receiving element (the electrodes are also referred to as pixel electrodes) are preferably provided on the same plane. It is further preferable that the other electrode of the light-emitting element and the other electrode of the light-receiving element be an electrode (also referred to as a common electrode) formed using one continuous conductive layer. It is still further preferable that the light-emitting element and the light-receiving element include a common layer. Thus, the manufacturing process of the light-emitting element and the light-receiving element can be simplified, so that the manufacturing cost can be reduced and the manufacturing yield can be increased.

More specific examples are described below with reference to drawings.

Structure Example 1 of Display Panel

Structure Example 1-1

Figure 6A:
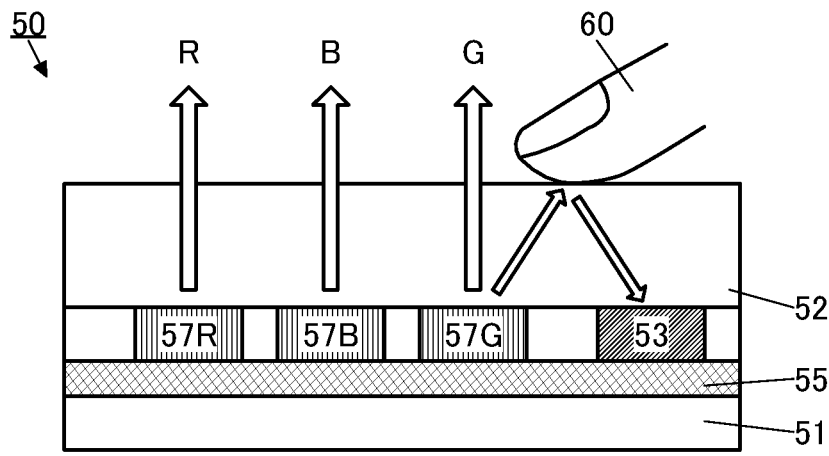
FIG. 6A, FIG. 6B, FIG. 6D, and FIG. 6F to FIG. 6H are diagrams illustrating structure examples of a display device.

A schematic view of a display panel 50 is illustrated in FIG. 6A. The display panel 50 includes a substrate 51, a substrate 52, a light-receiving element 53, a light-emitting element 57R, a light-emitting element 57G, a light-emitting element 57B, a functional layer 55, and the like.

The light-emitting element 57R, the light-emitting element 57G, the light-emitting element 57B, and the light-receiving element 53 are provided between the substrate 51 and the substrate 52.

The light-emitting element 57R, the light-emitting element 57G, and the light-emitting element 57B emit red (R) light, green (G) light, and blue (B) light, respectively.

The display panel 50 includes a plurality of pixels arranged in a matrix. One pixel includes one or more subpixels. One subpixel includes one light-emitting element. For example, the pixel can have a structure including three subpixels (e.g., three colors of R, G, and B or three colors of yellow (Y), cyan (C), and magenta (M)) or four subpixels (e.g., four colors of R, G, B, and white (W) or four colors of R, G, B, and Y). The pixel further includes the light-receiving element 53. The light-receiving element 53 may be provided in all the pixels or may be provided in some of the pixels. In addition, one pixel may include a plurality of light-receiving elements 53.

FIG. 6A illustrates a state where a finger 60 touches a surface of the substrate 52. Part of light emitted from the light-emitting element 57G is reflected or scattered by a contact portion of the substrate 52 and the finger 60. Then, part of the reflected light or scattered light enters the light-receiving element 53, and the contact of the finger 60 with the substrate 52 can be detected. That is, the display panel 50 can function as a touch panel.

The functional layer 55 includes a circuit that drives the light-emitting element 57R, the light-emitting element 57G, and the light-emitting element 57B and a circuit that drives the light-receiving element 53. The functional layer 55 is provided with a switch, a transistor, a capacitor, a wiring, and the like. Note that in the case where the light-emitting element 57R, the light-emitting element 57G, the light-emitting element 57B, and the light-receiving element 53 are driven by a passive-matrix method, a structure not provided with a switch or a transistor may be employed.

Figure 6B:
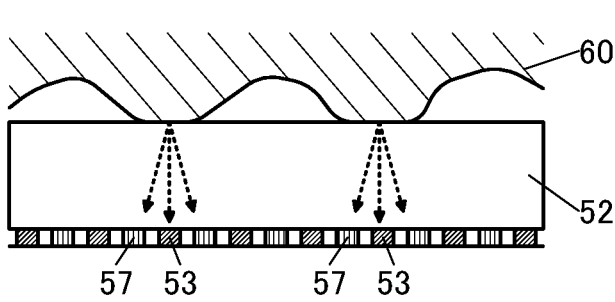

The display panel 50 may have a function of detecting a fingerprint of the finger 60. FIG. 6B schematically illustrates an enlarged view of the contact portion in a state where the finger 60 touches the substrate 52. FIG. 6B illustrates light-emitting elements 57 and the light-receiving elements 53 that are alternately arranged.

The fingerprint of the finger 60 is formed of depressions and projections. Therefore, as illustrated in FIG. 6B, the projections of the fingerprint touch the substrate 52, and scattered light (indicated by dashed arrows) occurs at the contact surfaces.

As illustrated in FIG. 6B, in the intensity distribution of the scattered light on the surface of the substrate 52 in contact with the finger 60, the intensity of light almost perpendicular to the contact surface is the highest, and the intensity of light becomes lower as an angle becomes larger in an oblique direction. Thus, the intensity of light received by the light-receiving element 53 positioned directly below the contact surface (i.e., overlapping with the contact surface) is the highest. Of the scattered light, light at greater than or equal to a predetermined scattering angle is fully reflected at the other surface (a surface opposite to the contact surface) of the substrate 52 and does not reach the light-receiving element 53 side. As a result, a clear fingerprint image can be captured.

In the case where an arrangement interval between the light-receiving elements 53 is smaller than a distance between two projections of a fingerprint, preferably a distance between a depression and a projection adjacent to each other, a clear fingerprint image can be obtained. The distance between a depression and a projection of a human's fingerprint is approximately 200 µm; thus, the arrangement interval between the light-receiving elements 53 is, for example, less than or equal to 400 µm, preferably less than or equal to 200 µm, further preferably less than or equal to 150 µm, still further preferably less than or equal to 100 µm, even still further preferably less than or equal to 50 µm and greater than or equal to 1 µm, preferably greater than or equal to 10 µm, further preferably greater than or equal to 20 µm.

Figure 6C:
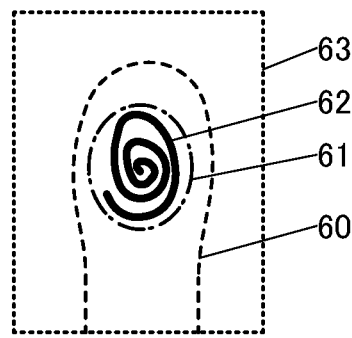
FIG. 6C and FIG. 6E are diagrams illustrating examples of images.

FIG. 6C illustrates an example of a fingerprint image captured with the display panel 50. In an image-capturing range 63 in FIG. 6C, the outline of the finger 60 is indicated by a dashed line and the outline of a contact portion 61 is indicated by a dashed-dotted line. In the contact portion 61, a high-contrast image of a fingerprint 62 can be captured owing to a difference in the amount of light incident on the light-receiving elements 53.

Figure 6D:
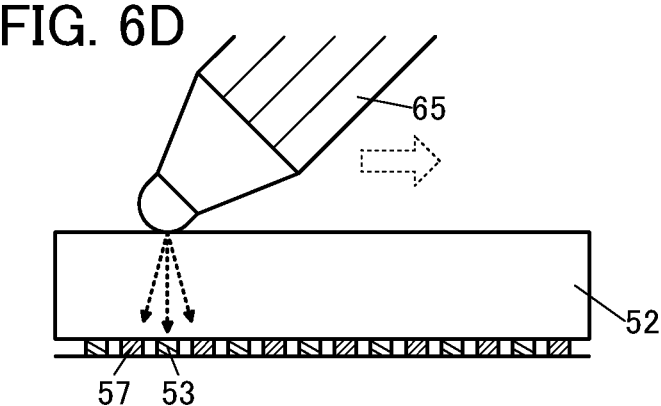

The display panel 50 can also function as a touch panel or a pen tablet. FIG. 6D illustrates a state where a tip of a stylus 65 slides in a direction indicated by a dashed arrow while the tip of the stylus 65 touches the substrate 52.

As illustrated in FIG. 6D, when light scattered by the contact surface of the tip of the stylus 65 and the substrate 52 enters the light-receiving element 53 that overlaps with the contact surface, the position of the tip of the stylus 65 can be detected with high accuracy.

Figure 6E:
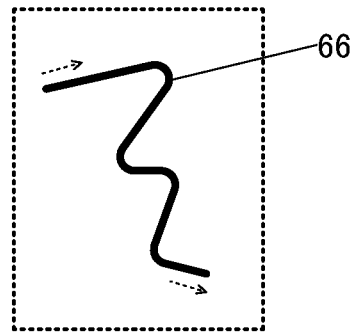

FIG. 6E illustrates an example of a path 66 of the stylus 65 that is detected by the display panel 50. The display panel 50 can detect the position of an object to be detected, such as the stylus 65, with high position accuracy, so that high-definition drawing can be performed using a drawing application or the like. Unlike the case of using a capacitive touch sensor, an electromagnetic induction touch pen, or the like, the position detection can be performed even when the stylus 65 is an object with high insulating properties; thus, the material of a tip portion of the stylus 65 is not limited, and a variety of writing materials (e.g., a brush, a glass pen, a quill pen, and the like) can be used.

Figure 6F:
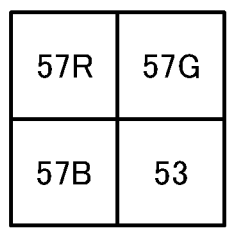
Figure 6G:
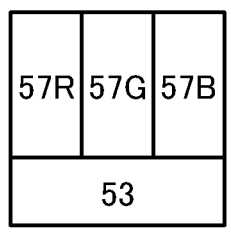
Figure 6H:
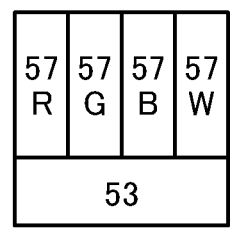

Here, FIG. 6F to FIG. 6H illustrate examples of a pixel that can be used in the display panel 50.

Pixels illustrated in FIG. 6F and FIG. 6G include the light-emitting element 57R for red (R), the light-emitting element 57G for green (G), the light-emitting element 57B for blue (B), and the light-receiving element 53. The pixels each include a pixel circuit for driving the light-emitting element 57R, the light-emitting element 57G, the light-emitting element 57B, and the light-receiving element 53.

FIG. 6F illustrates an example in which three light-emitting elements and one light-receiving element are provided in a matrix of 2×2. FIG. 6G illustrates an example in which three light-emitting elements are arranged in one line and one laterally long light-receiving element 53 is provided below the three light-emitting elements.

The pixel illustrated in FIG. 6H is an example including a light-emitting element 57W for white (W). Here, four light-emitting elements are arranged in one line and the light-receiving element 53 is provided below the four light-emitting elements.

Note that the pixel structure is not limited to the above structure, and a variety of arrangement methods can be employed.

Structure Example 1-2

An example of a structure including a light-emitting element emitting visible light, a light-emitting element emitting infrared light, and a light-receiving element is described below.

Figure 7A:
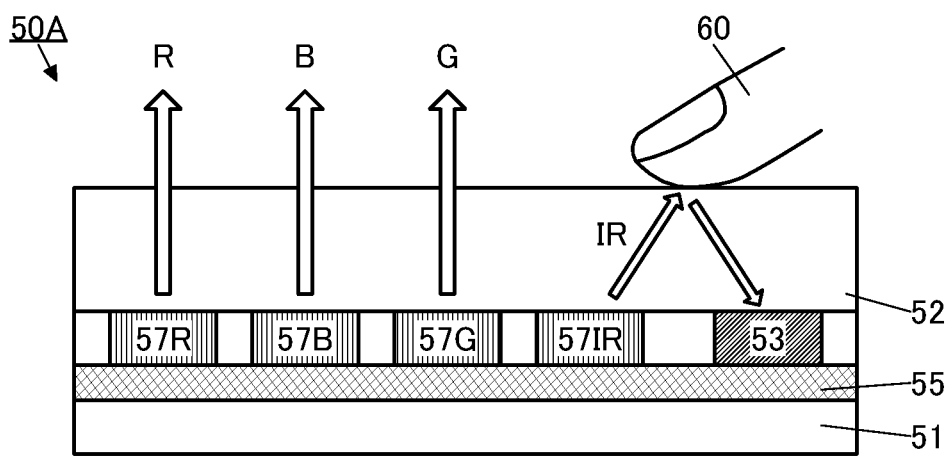
FIG. 7A to FIG. 7D are diagrams illustrating structure examples of a display device.

A display panel 50A illustrated in FIG. 7A includes a light-emitting element 57IR in addition to the components illustrated in FIG. 6A as an example. The light-emitting element 57IR is a light-emitting element emitting infrared light IR. Moreover, in that case, an element capable of receiving at least the infrared light IR emitted from the light-emitting element 57IR is preferably used as the light-receiving element 53. As the light-receiving element 53, an element capable of receiving both visible light and infrared light is further preferably used.

As illustrated in FIG. 7A, when the finger 60 touches the substrate 52, the infrared light IR emitted from the light-emitting element 57IR is reflected or scattered by the finger 60 and part of reflected light or scattered light enters the light-receiving element 53, so that the positional information of the finger 60 can be obtained.

Figure 7B:
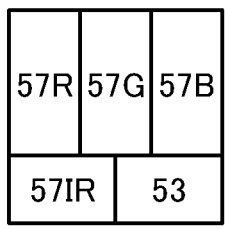
Figure 7C:
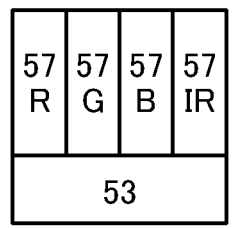
Figure 7D:
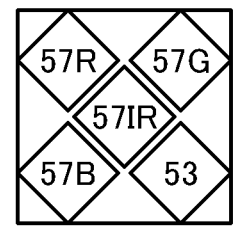

FIG. 7B to FIG. 7D illustrate examples of a pixel that can be used in the display panel 50A.

FIG. 7B illustrates an example in which three light-emitting elements are arranged in one line and the light-emitting element 57IR and the light-receiving element 53 are arranged below the three light-emitting elements in a horizontal direction. FIG. 6C illustrates an example in which four light-emitting elements including the light-emitting element 57IR are arranged in one line and the light-receiving element 53 is provided below the four light-emitting elements.

FIG. 7C illustrates an example in which three light-emitting elements and the light-receiving element 53 arranged in all directions with the light-emitting element 57IR used as a center.

Note that in the pixels illustrated in FIG. 7B to FIG. 7D, the light-emitting elements can be interchanged with each other, or the light-emitting element and the light-receiving element can be interchanged with each other.

The above is the description of Structure example 2.

Structure Example 2 of Display Panel

Structure Example 2-1

Figure 8A:
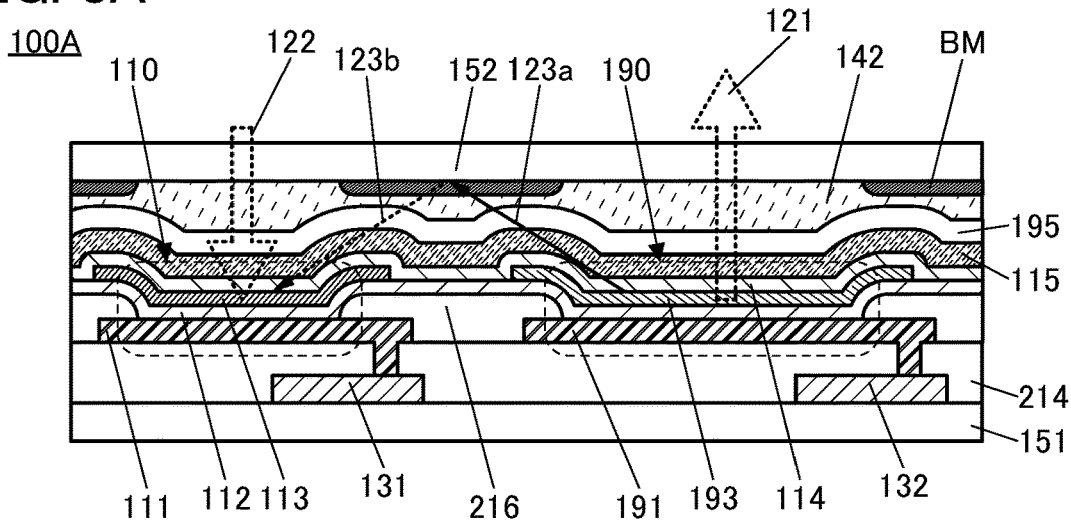
FIG. 8A to FIG. 8C are diagrams illustrating structure examples of display devices.

FIG. 8A is a schematic cross-sectional view of a display panel 100A.

The display panel 100A includes a light-receiving element 110 and a light-emitting element 190. The light-receiving element 110 includes a pixel electrode 111, a common layer 112, an active layer 113, a common layer 114, and a common electrode 115. The light-emitting element 190 includes a pixel electrode 191, the common layer 112, a light-emitting layer 193, the common layer 114, and the common electrode 115.

The pixel electrode 111, the pixel electrode 191, the common layer 112, the active layer 113, the light-emitting layer 193, the common layer 114, and the common electrode 115 may each have a single-layer structure or a stacked-layer structure.

The pixel electrode 111 and the pixel electrode 191 are positioned over an insulating layer 214. The pixel electrode 111 and the pixel electrode 191 can be formed using the same material in the same step.

The common layer 112 is positioned over the pixel electrode 111 and the pixel electrode 191. The common layer 112 is a layer shared by the light-receiving element 110 and the light-emitting element 190.

The active layer 113 overlaps with the pixel electrode 111 with the common layer 112 therebetween. The light-emitting layer 193 overlaps with the pixel electrode 191 with the common layer 112 therebetween. The active layer 113 includes a first organic compound, and the light-emitting layer 193 includes a second organic compound that is different from the first organic compound.

The common layer 114 is positioned over the common layer 112, the active layer 113, and the light-emitting layer 193. The common layer 114 is a layer shared by the light-receiving element 110 and the light-emitting element 190.

The common electrode 115 includes a portion overlapping with the pixel electrode 111 with the common layer 112, the active layer 113, and the common layer 114 therebetween. The common electrode 115 further includes a portion overlapping with the pixel electrode 191 with the common layer 112, the light-emitting layer 193, and the common layer 114 therebetween. The common electrode 115 is a layer shared by the light-receiving element 110 and the light-emitting element 190.

In the display panel of this embodiment, an organic compound is used for the active layer 113 of the light-receiving element 110. In the light-receiving element 110, the layers other than the active layer 113 can have structures in common with the layers in the light-emitting element 190 (EL element). Therefore, the light-receiving element 110 can be formed concurrently with the formation of the light-emitting element 190 only by adding a step of depositing the active layer 113 in the manufacturing process of the light-emitting element 190. The light-emitting element 190 and the light-receiving element 110 can be formed over one substrate. Accordingly, the light-receiving element 110 can be incorporated into the display panel without a significant increase in the number of manufacturing steps.

The display panel 100A illustrates an example in which the light-receiving element 110 and the light-emitting element 190 have a common structure except that the active layer 113 of the light-receiving element 110 and the light-emitting layer 193 of the light-emitting element 190 are separately formed. Note that the structures of the light-receiving element 110 and the light-emitting element 190 are not limited thereto. The light-receiving element 110 and the light-emitting element 190 may include separately formed layers other than the active layer 113 and the light-emitting layer 193 (see display panels 100D, 100E, and 100F described later). The light-receiving element 110 and the light-emitting element 190 preferably include at least one layer used in common (common layer). Thus, the light-receiving element 110 can be incorporated into the display panel without a significant increase in the number of manufacturing steps.

The display panel 100A includes the light-receiving element 110, the light-emitting element 190, a transistor 131, a transistor 132, and the like between a pair of substrates (a substrate 151 and a substrate 152).

In the light-receiving element 110, the common layer 112, the active layer 113, and the common layer 114, which are positioned between the pixel electrode 111 and the common electrode 115, can each also be referred to as an organic layer (a layer including an organic compound). The pixel electrode 111 preferably has a function of reflecting visible light. An end portion of the pixel electrode 111 is covered with a bank 216. The common electrode 115 has a function of transmitting visible light.

The light-receiving element 110 has a function of detecting light. Specifically, the light-receiving element 110 is a photoelectric conversion element that receives light 122 entering from the outside through the substrate 152 and converts the light 122 into an electrical signal.

A light-blocking layer BM is provided on a surface of the substrate 152 that faces the substrate 151. The light-blocking layer BM has an opening in a position overlapping with the light-receiving element 110 and in a position overlapping with the light-emitting element 190. Providing the light-blocking layer BM can control the range where the light-receiving element 110 detects light.

For the light-blocking layer BM, a material that blocks light emitted from the light-emitting element can be used. The light-blocking layer BM preferably absorbs visible light. As the light-blocking layer BM, a black matrix can be formed using a metal material or a resin material containing pigment (e.g., carbon black) or dye, for example. The light-blocking layer BM may have a stacked-layer structure of a red color filter, a green color filter, and a blue color filter.

Here, part of light emitted from the light-emitting element 190 is reflected in the display panel 100A and enters the light-receiving element 110 in some cases. The light-blocking layer BM can reduce the influence of such stray light. For example, in the case where the light-blocking layer BM is not provided, light 123a emitted from the light-emitting element 190 is reflected by the substrate 152 and reflected light 123b enters the light-receiving element 110 in some cases. Providing the light-blocking layer BM can inhibit the reflected light 123b from entering the light-receiving element 110. Consequently, noise can be reduced, and the sensitivity of a sensor using the light-receiving element 110 can be increased.

In the light-emitting element 190, the common layer 112, the light-emitting layer 193, and the common layer 114, which are positioned between the pixel electrode 191 and the common electrode 115, can each also be referred to as an EL layer. The pixel electrode 191 preferably has a function of reflecting visible light. An end portion of the pixel electrode 191 is covered with the bank 216. The pixel electrode 111 and the pixel electrode 191 are electrically insulated from each other by the bank 216. The common electrode 115 has a function of transmitting visible light.

The light-emitting element 190 has a function of emitting visible light. Specifically, the light-emitting element 190 is an electroluminescent element that emits light 121 to the substrate 152 side when voltage is applied between the pixel electrode 191 and the common electrode 115.

It is preferable that the light-emitting layer 193 be formed not to overlap with a light-receiving region of the light-receiving element 110. This inhibits the light-emitting layer 193 from absorbing the light 122, increasing the amount of light with which the light-receiving element 110 is irradiated.

The pixel electrode 111 is electrically connected to a source or a drain of the transistor 131 through an opening provided in the insulating layer 214. The end portion of the pixel electrode 111 is covered with the bank 216.

The pixel electrode 191 is electrically connected to a source or a drain of the transistor 132 through an opening provided in the insulating layer 214. The end portion of the pixel electrode 191 is covered with the bank 216. The transistor 132 has a function of controlling the driving of the light-emitting element 190.

The transistor 131 and the transistor 132 are on and in contact with the same layer (the substrate 151 in FIG. 8A).

At least part of a circuit electrically connected to the light-receiving element 110 and a circuit electrically connected to the light-emitting element 190 are preferably formed using the same material in the same step. Thus, the thickness of the display panel can be reduced and the manufacturing process can be simplified compared to the case where the two circuits are separately formed.

The light-receiving element 110 and the light-emitting element 190 are preferably covered with a protective layer 195. In FIG. 8A, the protective layer 195 is provided on and in contact with the common electrode 115. Providing the protective layer 195 can inhibit entry of impurities such as water into the light-receiving element 110 and the light-emitting element 190, so that the reliability of the light-receiving element 110 and the light-emitting element 190 can be increased. The protective layer 195 and the substrate 152 are bonded to each other with an adhesive layer 142.

Figure 9A:
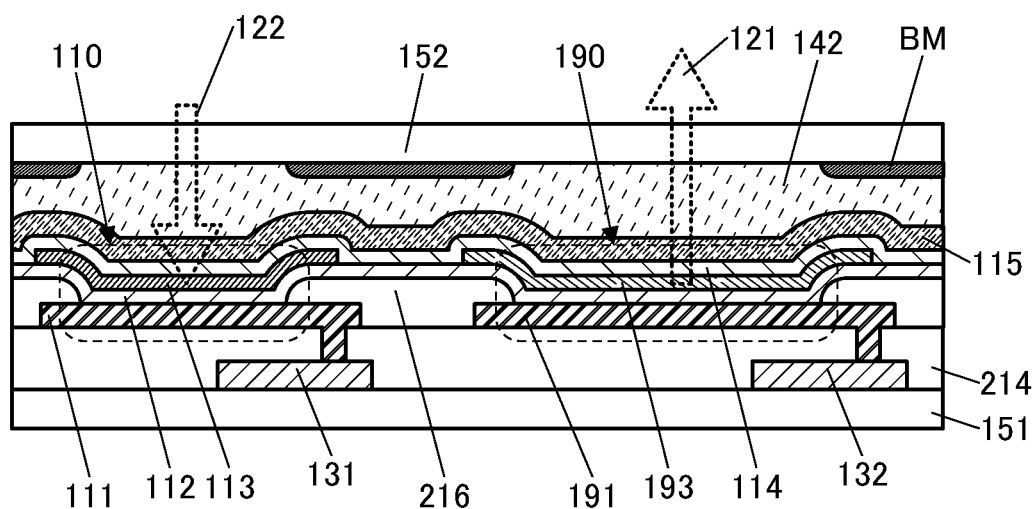
FIG. 9A and FIG. 9B are diagrams illustrating structure examples of a display device.

Note that as illustrated in FIG. 9A, the protective layer is not necessarily provided over the light-receiving element 110 and the light-emitting element 190. In FIG. 9A, the common electrode 115 and the substrate 152 are bonded to each other with the adhesive layer 142.

Figure 9B:
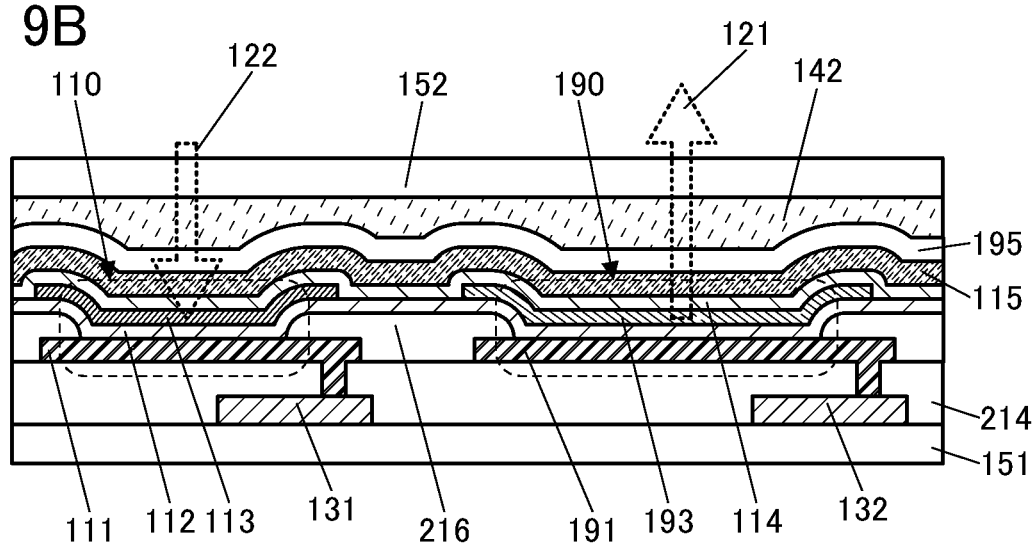

A structure that does not include the light-blocking layer BM as illustrated in FIG. 9B may be employed. This can increase the light-receiving area of the light-receiving element 110, further increasing the sensitivity of the sensor.

Structure Example 2-2

Figure 8B:
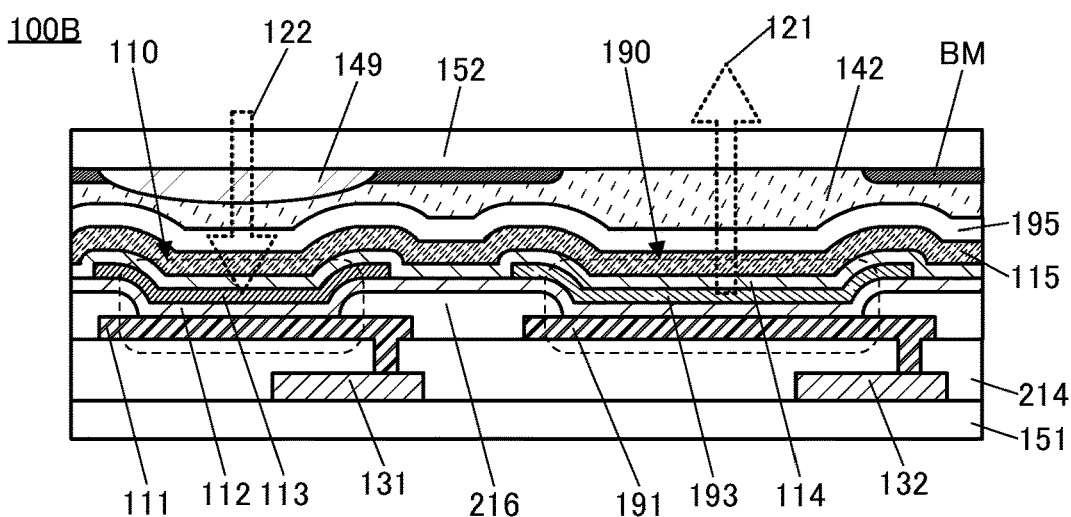

FIG. 8B illustrates a cross-sectional view of a display panel 100B. Note that in the description of the display panel below, components similar to those of the above-mentioned display panel are not described in some cases.

The display panel 100B illustrated in FIG. 8B includes a lens 149 in addition to the components of the display panel 100A.

The lens 149 is provided in a position overlapping with the light-receiving element 110. In the display panel 100B, the lens 149 is provided in contact with the substrate 152. The lens 149 included in the display panel 100B is a convex lens having a convex surface on the substrate 151 side. Note that a convex lens having a convex surface on the substrate 152 side may be provided in a region overlapping with the light-receiving element 110.

In the case where both the light-blocking layer BM and the lens 149 are formed on the same plane of the substrate 152, their formation order is not limited. FIG. 8B illustrates an example in which the lens 149 is formed first; alternatively, the light-blocking layer BM may be formed first. In FIG. 8B, an end portion of the lens 149 is covered with the light-blocking layer BM.

The display panel 100B has a structure in which the light 122 enters the light-receiving element 110 through the lens 149. With the lens 149, the amount of the light 122 incident on the light-receiving element 110 can be increased compared to the case where the lens 149 is not provided. This can increase the sensitivity of the light-receiving element 110.

As a method for forming the lens used in the display panel of this embodiment, a lens such as a microlens may be formed directly over the substrate or the light-receiving element, or a lens array formed separately, such as a microlens array, may be bonded to the substrate.

Structure Example 2-3

Figure 8C:
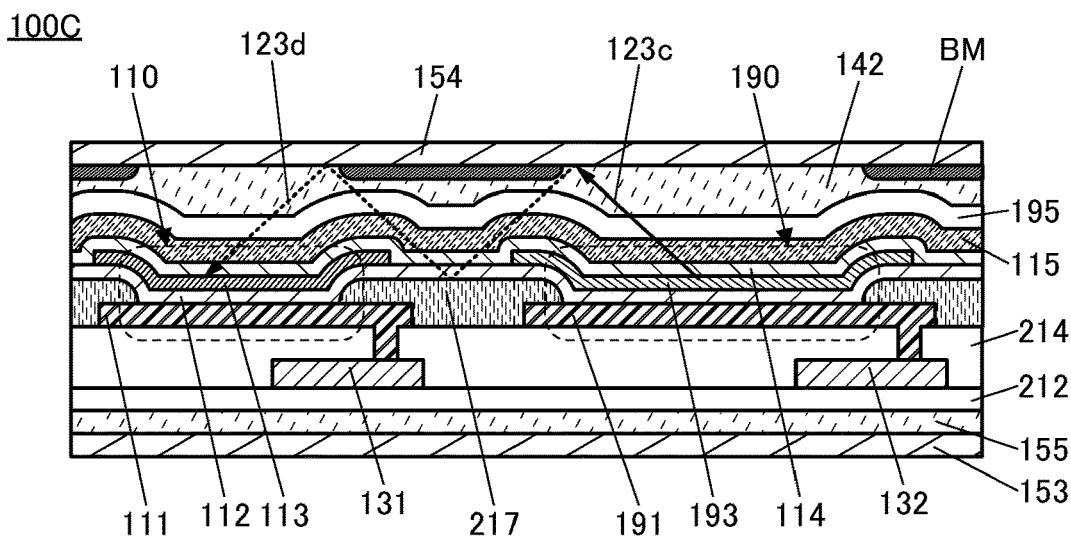

FIG. 8C illustrates a schematic cross-sectional view of a display panel 100C. The display panel 100C is different from the display panel 100A in that the substrate 151, the substrate 152, and the bank 216 are not included and a substrate 153, a substrate 154, an adhesive layer 155, an insulating layer 212, and a bank 217 are included.

The substrate 153 and the insulating layer 212 are bonded to each other with the adhesive layer 155. The substrate 154 and the protective layer 195 are bonded to each other with the adhesive layer 142.

The display panel 100C has a structure obtained in such a manner that the insulating layer 212, the transistor 131, the transistor 132, the light-receiving element 110, the light-emitting element 190, and the like are formed over a formation substrate and then transferred onto the substrate 153. The substrate 153 and the substrate 154 preferably have flexibility. Accordingly, the flexibility of the display panel 100C can be increased. For example, a resin is preferably used for each of the substrate 153 and the substrate 154.

For each of the substrate 153 and the substrate 154, a polyester resin such as polyethylene terephthalate (PET) or polyethylene naphthalate (PEN), a polyacrylonitrile resin, an acrylic resin, a polyimide resin, a polymethyl methacrylate resin, a polycarbonate (PC) resin, a polyether sulfone (PES) resin, a polyamide resin (e.g., nylon or aramid), a polysiloxane resin, a cycloolefin resin, a polystyrene resin, a polyamide-imide resin, a polyurethane resin, a polyvinyl chloride resin, a polyvinylidene chloride resin, a polypropylene resin, a polytetrafluoroethylene (PTFE) resin, an ABS resin, or cellulose nanofiber can be used, for example. Glass that is thin enough to have flexibility may be used for one or both of the substrate 153 and the substrate 154.

As the substrate included in the display panel of this embodiment, a film having high optical isotropy may be used. Examples of the film having high optical isotropy include a triacetyl cellulose (TAC, also referred to as cellulose triacetate) film, a cycloolefin polymer (COP) film, a cycloolefin copolymer (COC) film, and an acrylic film.

The bank 217 preferably absorbs light emitted by the light-emitting element. As the bank 217, a black matrix can be formed using a resin material containing a pigment or dye, for example. Moreover, the bank 217 can be formed of a colored insulating layer by using a brown resist material.

In some cases, light 123c emitted by the light-emitting element 190 is reflected by the substrate 152 and the bank 217 and reflected light 123d enters the light-receiving element 110. In other cases, the light 123c passes through the bank 217 and is reflected by a transistor, a wiring, or the like, and thus reflected light enters the light-receiving element 110. When the bank 217 absorbs the light 123c, the reflected light 123d can be inhibited from entering the light-receiving element 110. Consequently, noise can be reduced, and the sensitivity of a sensor using the light-receiving element 110 can be increased.

The bank 217 preferably absorbs at least light having a wavelength that is detected by the light-receiving element 110. For example, in the case where the light-receiving element 110 detects red light emitted by the light-emitting element 190, the bank 217 preferably absorbs at least red light. For example, when the bank 217 includes a blue color filter, the bank 217 can absorb the red light 123c and thus the reflected light 123d can be inhibited from entering the light-receiving element 110.

Structure Example 2-4

Although the light-emitting element and the light-receiving element include two common layers in the above examples, one embodiment of the present invention is not limited thereto. Examples in which common layers have different structures are described below.

Figure 10A:
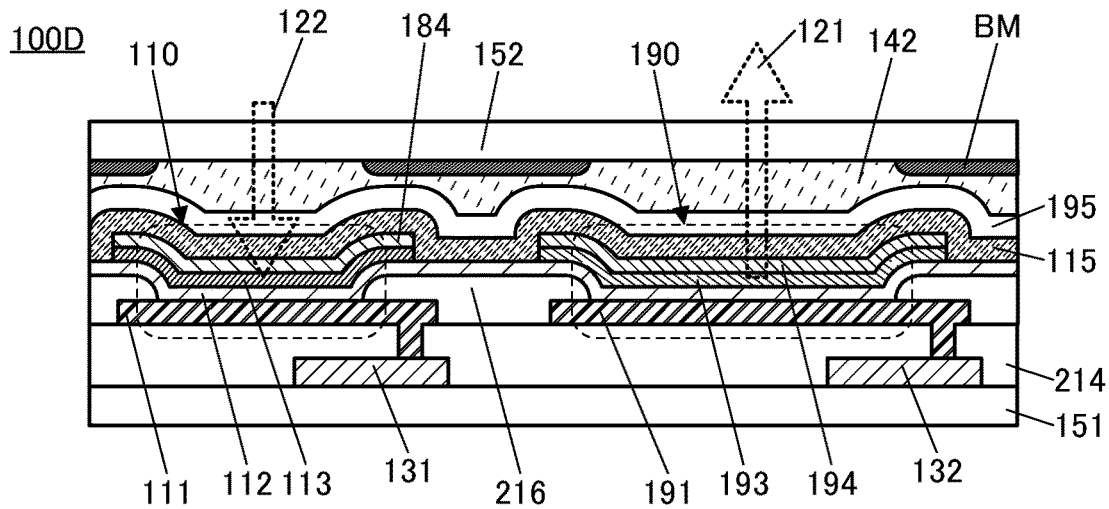
FIG. 10A to FIG. 10C are diagrams illustrating structure examples of display devices.

FIG. 10A illustrates a schematic cross-sectional view of a display panel 100D. The display panel 100D is different from the display panel 100A in that the common layer 114 is not included and a buffer layer 184 and a buffer layer 194 are included. The buffer layer 184 and the buffer layer 194 may each have a single-layer structure or a stacked-layer structure.

In the display panel 100D, the light-receiving element 110 includes the pixel electrode 111, the common layer 112, the active layer 113, the buffer layer 184, and the common electrode 115. In the display panel 100D, the light-emitting element 190 includes the pixel electrode 191, the common layer 112, the light-emitting layer 193, the buffer layer 194, and the common electrode 115.

The display panel 100D shows an example in which the buffer layer 184 between the common electrode 115 and the active layer 113 and the buffer layer 194 between the common electrode 115 and the light-emitting layer 193 are formed separately. As the buffer layer 184 and the buffer layer 194, one or both of an electron-injection layer and an electron-transport layer can be formed, for example.

Figure 10B:
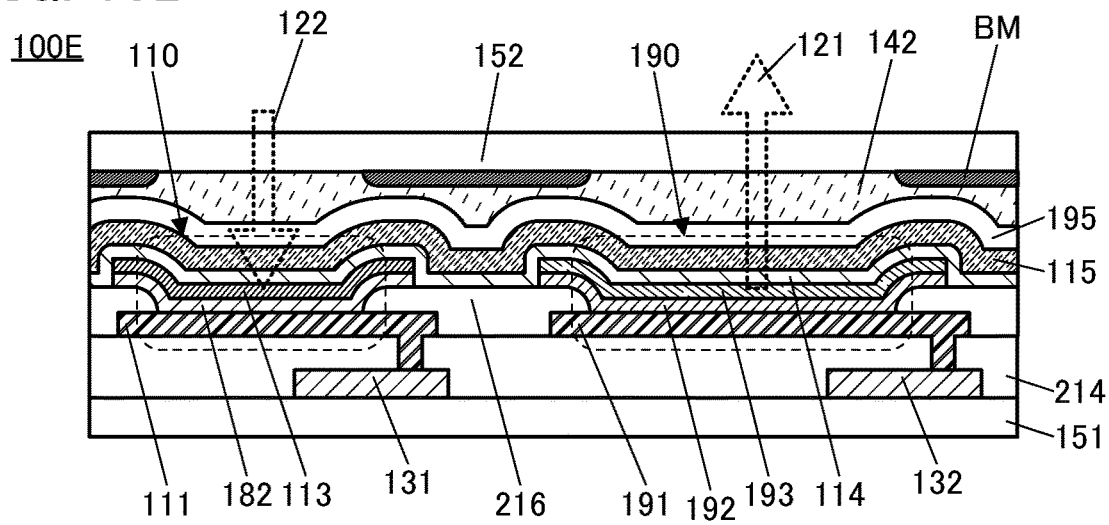

FIG. 10B illustrates a schematic cross-sectional view of a display panel 100E. The display panel 100E is different from the display panel 100A in that the common layer 112 is not included and a buffer layer 182 and a buffer layer 192 are included. The buffer layer 182 and the buffer layer 192 may each have a single-layer structure or a stacked-layer structure.

In the display panel 100E, the light-receiving element 110 includes the pixel electrode 111, the buffer layer 182, the active layer 113, the common layer 114, and the common electrode 115. In the display panel 100E, the light-emitting element 190 includes the pixel electrode 191, the buffer layer 192, the light-emitting layer 193, the common layer 114, and the common electrode 115.

The display panel 100E shows an example in which the buffer layer 182 between the pixel electrode 111 and the active layer 113 and the buffer layer 192 between the pixel electrode 191 and the light-emitting layer 193 are formed separately. As the buffer layer 182 and the buffer layer 192, one or both of a hole-injection layer and a hole-transport layer can be formed, for example.

Figure 10C:
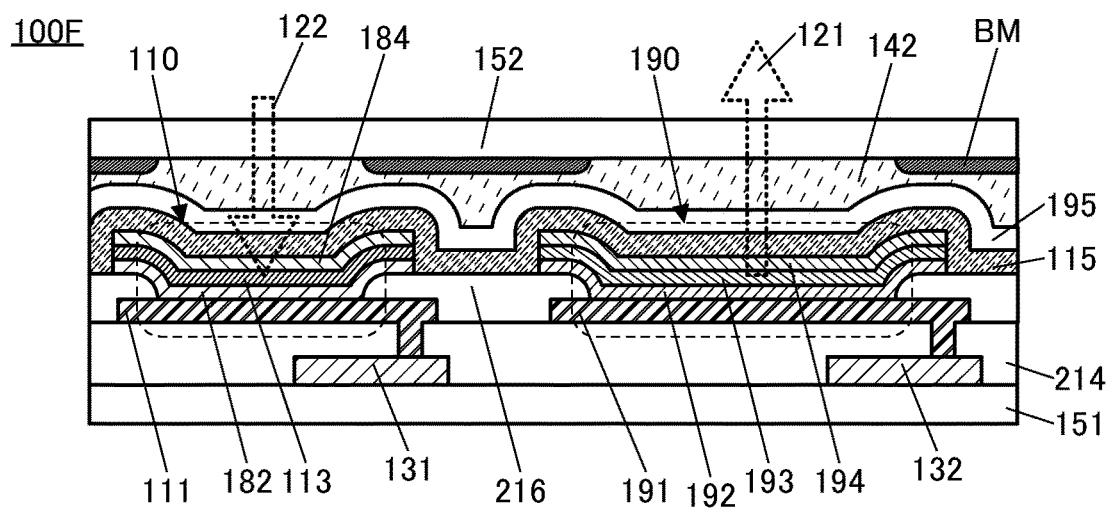

FIG. 10C illustrates a schematic cross-sectional view of a display panel 100F. The display panel 100F is different from the display panel 100A in that the common layer 112 and the common layer 114 are not included and the buffer layer 182, the buffer layer 184, the buffer layer 192, and the buffer layer 194 are included.

In the display panel 100F, the light-receiving element 110 includes the pixel electrode 111, the buffer layer 182, the active layer 113, the buffer layer 184, and the common electrode 115. In the display panel 100F, the light-emitting element 190 includes the pixel electrode 191, the buffer layer 192, the light-emitting layer 193, the buffer layer 194, and the common electrode 115.

In the formation of the light-receiving element 110 and the light-emitting element 190, not only the active layer 113 and the light-emitting layer 193 but also other layers can be formed separately.

The display panel 100F shows an example in which the light-receiving element 110 and the light-emitting element 190 do not have a common layer between the pair of electrodes (the pixel electrode 111 or the pixel electrode 191 and the common electrode 115). The light-receiving element 110 and the light-emitting element 190 included in the display panel 100F can be formed in the following manner: the pixel electrode 111 and the pixel electrode 191 are formed over the insulating layer 214 using the same material in the same step; the buffer layer 182, the active layer 113, and the buffer layer 184 are formed over the pixel electrode 111, and the buffer layer 192, the light-emitting layer 193, and the buffer layer 194 are formed over the pixel electrode 191; and then, the common electrode 115 is formed to cover the buffer layer 184, the buffer layer 194, and the like.

Note that the formation order of the stacked-layer structure of the buffer layer 182, the active layer 113, and the buffer layer 184 and the stacked-layer structure of the buffer layer 192, the light-emitting layer 193, and the buffer layer 194 is not particularly limited. For example, after the buffer layer 182, the active layer 113, and the buffer layer 184 are deposited, the buffer layer 192, the light-emitting layer 193, and the buffer layer 194 may be deposited. In contrast, the buffer layer 192, the light-emitting layer 193, and the buffer layer 194 may be deposited before the buffer layer 182, the active layer 113, and the buffer layer 184 are deposited. Alternate deposition of the buffer layer 182, the buffer layer 192, the active layer 113, the light-emitting layer 193, and the like in this order is also possible.

Structure Example 3 of Display Panel

More specific structure examples of the display panel are described below.

Structure Example 3-1

Figure 11:
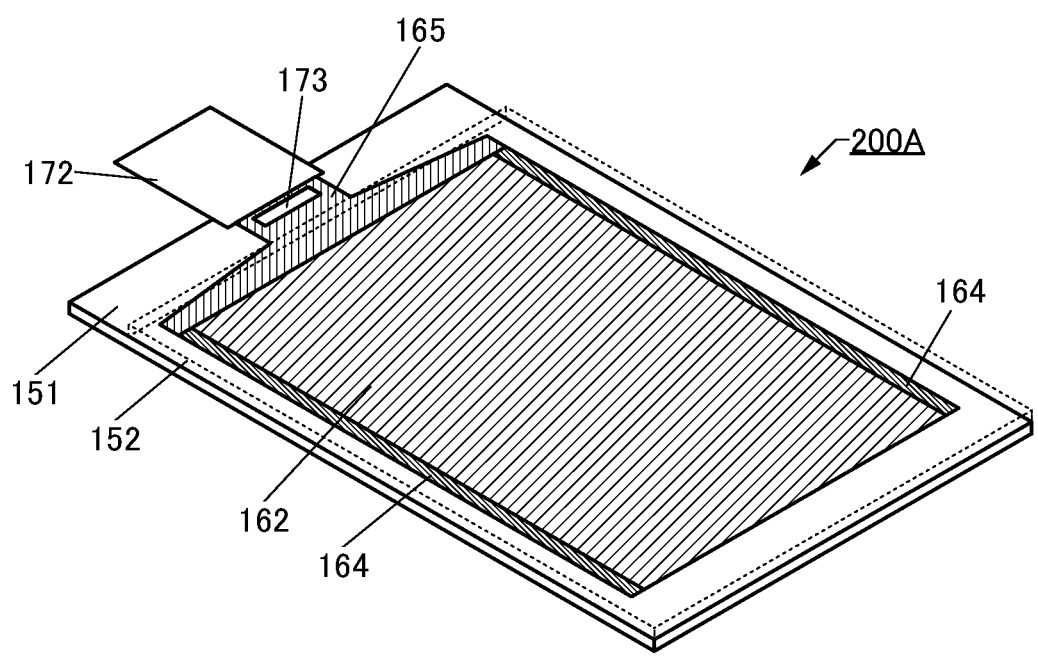
FIG. 11 is a diagram illustrating a structure example of a display device.

FIG. 11 illustrates a perspective view of a display panel 200A.

The display panel 200A has a structure in which the substrate 151 and the substrate 152 are bonded to each other. In FIG. 11, the substrate 152 is indicated by a dashed line.

The display panel 200A includes a display portion 162, a circuit 164, a wiring 165, and the like. FIG. 11 illustrates an example in which an IC (integrated circuit) 173 and an FPC 172 are mounted on the display panel 200A. Thus, the structure illustrated in FIG. 11 can be regarded as a display module including the display panel 200A, the IC, and the FPC.

As the circuit 164, a scan line driver circuit can be used.

The wiring 165 has a function of supplying a signal and power to the display portion 162 and the circuit 164. The signal and power are input to the wiring 165 from the outside through the FPC 172 or from the IC 173.

FIG. 11 illustrates an example in which the IC 173 is provided over the substrate 151 by a COG (Chip On Glass) method, a COF (Chip On Film) method, or the like. An IC including a scan line driver circuit, a signal line driver circuit, or the like can be used as the IC 173, for example. Note that the display panel 200A and the display module may have a structure that does not include an IC. The IC may be mounted on the FPC by a COF method or the like.

Figure 12:
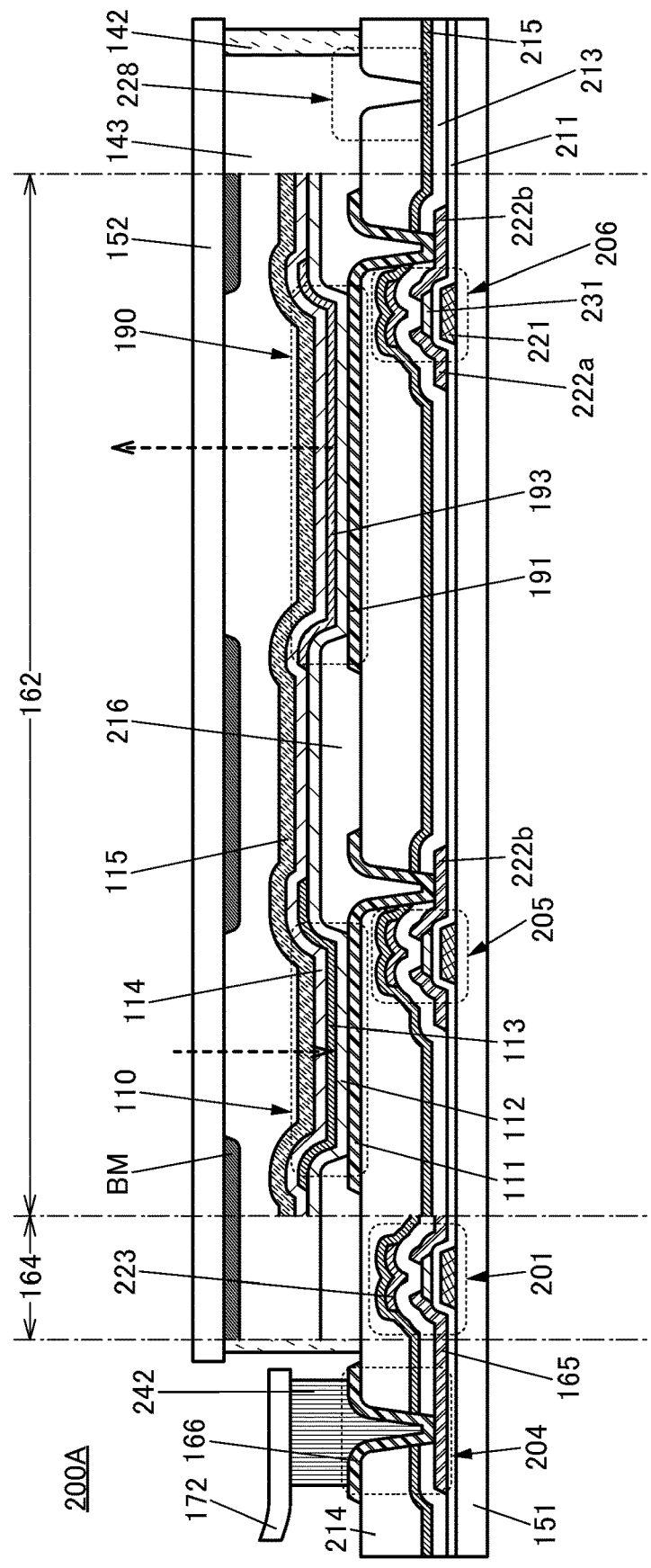
FIG. 12 is a diagram illustrating a structure example of a display device.

FIG. 12 illustrates an example of a cross section of part of a region including the FPC 172, part of a region including the circuit 164, part of a region including the display portion 162, and part of a region including an end portion of the display panel 200A illustrated in FIG. 11.

The display panel 200A illustrated in FIG. 12 includes a transistor 201, a transistor 205, a transistor 206, the light-emitting element 190, the light-receiving element 110, and the like between the substrate 151 and the substrate 152.

The substrate 152 and the insulating layer 214 are attached to each other with the adhesive layer 142. A solid sealing structure, a hollow sealing structure, or the like can be employed to seal the light-emitting element 190 and the light-receiving element 110. In FIG. 12, a space 143 surrounded by the substrate 152, the adhesive layer 142, and the insulating layer 214 is filled with an inert gas (e.g., nitrogen or argon), that is, a hollow sealing structure is employed. The adhesive layer 142 may be provided to overlap with the light-emitting element 190. The space 143 surrounded by the substrate 152, the adhesive layer 142, and the insulating layer 214 may be filled with a resin different from that of the adhesive layer 142.

The light-emitting element 190 has a stacked-layer structure in which the pixel electrode 191, the common layer 112, the light-emitting layer 193, the common layer 114, and the common electrode 115 are stacked in this order from the insulating layer 214 side. The pixel electrode 191 is connected to a conductive layer 222b included in the transistor 206 through an opening provided in the insulating layer 214. The transistor 206 has a function of controlling the driving of the light-emitting element 190. An end portion of the pixel electrode 191 is covered with the bank 216. The pixel electrode 191 includes a material that reflects visible light, and the common electrode 115 includes a material that transmits visible light.

The light-receiving element 110 has a stacked-layer structure in which the pixel electrode 111, the common layer 112, the active layer 113, the common layer 114, and the common electrode 115 are stacked in this order from the insulating layer 214 side. The pixel electrode 111 is electrically connected to the conductive layer 222b included in the transistor 205 through an opening provided in the insulating layer 214. An end portion of the pixel electrode 111 is covered with the bank 216. The pixel electrode 111 includes a material that reflects visible light, and the common electrode 115 includes a material that transmits visible light.

Light emitted from the light-emitting element 190 is emitted toward the substrate 152 side. Light enters the light-receiving element 110 through the substrate 152 and the space 143. For the substrate 152, a material that has high transmittance with respect to visible light is preferably used.

The pixel electrode 111 and the pixel electrode 191 can be formed using the same material in the same step. The common layer 112, the common layer 114, and the common electrode 115 are used in both the light-receiving element 110 and the light-emitting element 190. The light-receiving element 110 and the light-emitting element 190 can have common components except the active layer 113 and the light-emitting layer 193. Thus, the light-receiving element 110 can be incorporated into the display panel 100A without a significant increase in the number of manufacturing steps.

The light-blocking layer BM is provided on a surface of the substrate 152 that faces the substrate 151. The light-blocking layer BM has an opening in a position overlapping with the light-receiving element 110 and in a position overlapping with the light-emitting element 190. Providing the light-blocking layer BM can control the range where the light-receiving element 110 detects light. Furthermore, with the light-blocking layer BM, light from the light-emitting element 190 can be inhibited from directly entering the light-receiving element 110. Hence, a sensor with less noise and high sensitivity can be obtained.

The transistor 201, the transistor 205, and the transistor 206 are formed over the substrate 151. These transistors can be formed using the same materials in the same steps.

An insulating layer 211, an insulating layer 213, an insulating layer 215, and the insulating layer 214 are provided in this order over the substrate 151. Parts of the insulating layer 211 function as gate insulating layers of the transistors. Parts of the insulating layer 213 function as gate insulating layers of the transistors. The insulating layer 215 is provided to cover the transistors. The insulating layer 214 is provided to cover the transistors and has a function of a planarization layer. Note that there is no limitation on the number of gate insulating layers and the number of insulating layers covering the transistors, and each insulating layer may have either a single layer or two or more layers.

A material through which impurities such as water and hydrogen do not easily diffuse is preferably used for at least one of the insulating layers that cover the transistors. This allows the insulating layer to serve as a barrier layer. Such a structure can effectively inhibit diffusion of impurities into the transistors from the outside and increase the reliability of the display device.

An inorganic insulating film is preferably used as each of the insulating layer 211, the insulating layer 213, and the insulating layer 215. As the inorganic insulating film, for example, a silicon nitride film, a silicon oxynitride film, a silicon oxide film, a silicon nitride oxide film, an aluminum oxide film, an aluminum nitride film, or the like which is an inorganic insulating film can be used. A hafnium oxide film, an yttrium oxide film, a zirconium oxide film, a gallium oxide film, a tantalum oxide film, a magnesium oxide film, a lanthanum oxide film, a cerium oxide film, a neodymium oxide film, or the like may also be used. A stack including two or more of the above insulating films may also be used.

Here, an organic insulating film often has a lower barrier property than an inorganic insulating film. Therefore, the organic insulating film preferably has an opening in the vicinity of an end portion of the display panel 200A. This can inhibit diffusion of impurities from the end portion of the display panel 200A through the organic insulating film. Alternatively, in order to prevent the organic insulating film from being exposed at the end portion of the display panel 200A, the organic insulating film may be formed so that its end portion is positioned on the inner side compared to the end portion of the display panel 200A.

An organic insulating film is suitable for the insulating layer 214 functioning as a planarization layer. Examples of materials that can be used for the organic insulating film include an acrylic resin, a polyimide resin, an epoxy resin, a polyamide resin, a polyimide-amide resin, a siloxane resin, a benzocyclobutene-based resin, a phenol resin, and precursors of these resins.

In a region 228 illustrated in FIG. 12, an opening is formed in the insulating layer 214. This can inhibit diffusion of impurities into the display portion 162 from the outside through the insulating layer 214 even when an organic insulating film is used as the insulating layer 214. Thus, the reliability of the display panel 200A can be increased.

Each of the transistor 201, the transistor 205, and the transistor 206 includes a conductive layer 221 functioning as a gate, the insulating layer 211 functioning as the gate insulating layer, a conductive layer 222a and the conductive layer 222b functioning as a source and a drain, a semiconductor layer 231, the insulating layer 213 functioning as the gate insulating layer, and a conductive layer 223 functioning as a gate. Here, a plurality of layers obtained by processing the same conductive film are shown with the same hatching pattern. The insulating layer 211 is positioned between the conductive layer 221 and the semiconductor layer 231. The insulating layer 213 is positioned between the conductive layer 223 and the semiconductor layer 231.

There is no particular limitation on the structure of the transistors included in the display panel of this embodiment. For example, a planar transistor, a staggered transistor, or an inverted staggered transistor can be used. A top-gate or bottom-gate transistor structure may be employed. Alternatively, gates may be provided above and below a semiconductor layer where a channel is formed.

The structure in which the semiconductor layer where a channel is formed is provided between two gates is used for the transistor 201, the transistor 205, and the transistor 206. The two gates may be connected to each other and supplied with the same signal to drive the transistor. Alternatively, a potential for controlling the threshold voltage may be supplied to one of the two gates and a potential for driving may be supplied to the other to control the threshold voltage of the transistor.

There is no particular limitation on the crystallinity of a semiconductor material used for the transistors, and any of an amorphous semiconductor, a single crystal semiconductor, and a semiconductor having crystallinity other than single crystal (a microcrystalline semiconductor, a polycrystalline semiconductor, or a semiconductor partly including crystal regions) may be used. A single crystal semiconductor or a semiconductor having crystallinity is preferably used, in which case deterioration of the transistor characteristics can be inhibited.

A semiconductor layer of a transistor preferably includes a metal oxide (also referred to as an oxide semiconductor). Alternatively, the semiconductor layer of the transistor may include silicon. Examples of silicon include amorphous silicon and crystalline silicon (e.g., low-temperature polysilicon or single crystal silicon).

The semiconductor layer preferably includes indium, M (M is one or more kinds selected from gallium, aluminum, silicon, boron, yttrium, tin, copper, vanadium, beryllium, titanium, iron, nickel, germanium, zirconium, molybdenum, lanthanum, cerium, neodymium, hafnium, tantalum, tungsten, and magnesium), and zinc, for example. Specifically, M is preferably one or more kinds selected from aluminum, gallium, yttrium, and tin.

It is particularly preferable to use an oxide containing indium (In), gallium (Ga), and zinc (Zn) (also referred to as IGZO) for the semiconductor layer.

In the case where the semiconductor layer is an In-M-Zn oxide, a sputtering target used for depositing the In-M-Zn oxide preferably has the atomic ratio of In higher than or equal to the atomic ratio of M. Examples of the atomic ratio of the metal elements in such a sputtering target include In:M:Zn=1:1:1, In:M:Zn=1:1:1.2, In:M:Zn=2:1:3, In:M:Zn=3:1:2, In:M:Zn=4:2:3, In:M:Zn=4:2:4.1, In:M:Zn=5:1:3, In:M:Zn=5:1:6, In:M:Zn=5:1:7, In:M:Zn=5:1:8, In:M:Zn=6:1:6, and In:M:Zn=5:2:5.

A target including a polycrystalline oxide is preferably used as the sputtering target, in which case the semiconductor layer having crystallinity is easily formed. Note that the atomic ratio in the deposited semiconductor layer may vary from the above atomic ratio between metal elements in the sputtering target in a range of ±40%. For example, in the case where the composition of a sputtering target used for the semiconductor layer is In:Ga:Zn=4:2:4.1 [atomic ratio], the composition of the semiconductor layer to be deposited is sometimes in the neighborhood of In:Ga:Zn=4:2:3 [atomic ratio].

Note that when the atomic ratio is described as In:Ga:Zn=4:2:3 or in the neighborhood thereof, the case is included where Ga is greater than or equal to 1 and less than or equal to 3 and Zn is greater than or equal to 2 and less than or equal to 4 with In being 4. When the atomic ratio is described as In:Ga:Zn=5:1:6 or in the neighborhood thereof, the case is included where Ga is greater than 0.1 and less than or equal to 2 and Zn is greater than or equal to 5 and less than or equal to 7 with In being 5. When the atomic ratio is described as In:Ga:Zn=1:1:1 or in the neighborhood thereof, the case is included where Ga is greater than 0.1 and less than or equal to 2 and Zn is greater than 0.1 and less than or equal to 2 with In being 1.

The transistor included in the circuit 164 and the transistor included in the display portion 162 may have the same structure or different structures. A plurality of transistors included in the circuit 164 may have the same structure or two or more kinds of structures. Similarly, a plurality of transistors included in the display portion 162 may have the same structure or two or more kinds of structures.

A connection portion 204 is provided in a region of the substrate 151 that does not overlap with the substrate 152. In the connection portion 204, the wiring 165 is electrically connected to the FPC 172 via a conductive layer 166 and a connection layer 242. On a top surface of the connection portion 204, the conductive layer 166 obtained by processing the same conductive film as the pixel electrode 191 is exposed. Thus, the connection portion 204 and the FPC 172 can be electrically connected to each other through the connection layer 242.

A variety of optical members can be arranged on the outer surface of the substrate 152. Examples of the optical members include a polarizing plate, a retardation plate, a light diffusion layer (a diffusion film or the like), an anti-reflective layer, and a light-condensing film. Furthermore, an antistatic film inhibiting the attachment of dust, a water repellent film suppressing the attachment of stain, a hard coat film inhibiting generation of a scratch caused by the use, a shock absorbing layer, or the like may be provided on the outside of the substrate 152.

For each of the substrate 151 and the substrate 152, glass, quartz, ceramic, sapphire, a resin, or the like can be used. When a flexible material is used for the substrate 151 and the substrate 152, the flexibility of the display panel can be increased.

As the adhesive layer, a variety of curable adhesives, e.g., a photocurable adhesive such as an ultraviolet curable adhesive, a reactive curable adhesive, a thermosetting adhesive, and an anaerobic adhesive can be used. Examples of these adhesives include an epoxy resin, an acrylic resin, a silicone resin, a phenol resin, a polyimide resin, an imide resin, a PVC (polyvinyl chloride) resin, a PVB (polyvinyl butyral) resin, and an EVA (ethylene vinyl acetate) resin. In particular, a material with low moisture permeability, such as an epoxy resin, is preferred. Alternatively, a two-component resin may be used. An adhesive sheet or the like may be used.

As the connection layer 242, an anisotropic conductive film (ACF), an anisotropic conductive paste (ACP), or the like can be used.

The light-emitting element 190 may be of a top emission type, a bottom emission type, a dual emission type, or the like. A conductive film that transmits visible light is used as the electrode through which light is extracted. A conductive film that reflects visible light is preferably used as the electrode through which light is not extracted.

The light-emitting element 190 includes at least the light-emitting layer 193. The light-emitting element 190 may further include, as a layer other than the light-emitting layer 193, a layer containing a substance with a high hole-injection property, a substance with a high hole-transport property, a hole-blocking material, a substance with a high electron-transport property, a substance with a high electron-injection property, a substance with a bipolar property (a substance with a high electron- and hole-transport property), or the like. For example, the common layer 112 preferably includes one or both of a hole-injection layer and a hole-transport layer. For example, the common layer 114 preferably includes one or both of an electron-transport layer and an electron-injection layer.

The common layer 112, the light-emitting layer 193, and the common layer 114 may use either a low molecular compound or a high molecular compound and may also contain an inorganic compound. The layers that constitute the common layer 112, the light-emitting layer 193, and the common layer 114 can each be formed by a method such as an evaporation method (including a vacuum evaporation method), a transfer method, a printing method, an inkjet method, or a coating method.

The light-emitting layer 193 may contain an inorganic compound such as quantum dots as a light-emitting material.

The active layer 113 of the light-receiving element 110 includes a semiconductor. Examples of the semiconductor include an inorganic semiconductor such as silicon and an organic semiconductor including an organic compound. This embodiment shows an example in which an organic semiconductor is used as the semiconductor included in the active layer. The use of an organic semiconductor is preferable because the light-emitting layer 193 of the light-emitting element 190 and the active layer 113 of the light-receiving element 110 can be formed by the same method (e.g., a vacuum evaporation method) and thus the same manufacturing apparatus can be used.

Examples of an n-type semiconductor material included in the active layer 113 include electron-accepting organic semiconductor materials such as fullerene (e.g., $C_{60}$ and $C_{70}$) and derivatives thereof. As a p-type semiconductor material included in the active layer 113, an electron-donating organic semiconductor material such as copper(II) phthalocyanine (CuPc), tetraphenyldibenzoperiflanthene (DBP), or zinc phthalocyanine (ZnPc) can be given.

For example, the active layer 113 is preferably formed by co-evaporation of an n-type semiconductor and a p-type semiconductor.

As materials that can be used for a gate, a source, and a drain of a transistor and conductive layers such as a variety of wirings and electrodes included in a display panel, metals such as aluminum, titanium, chromium, nickel, copper, yttrium, zirconium, molybdenum, silver, tantalum, and tungsten, an alloy containing any of these metals as its main component, and the like can be given. A film containing any of these materials can be used in a single layer or as a stacked-layer structure.

As a light-transmitting conductive material, a conductive oxide such as indium oxide, indium tin oxide, indium zinc oxide, zinc oxide, or zinc oxide containing gallium, or graphene can be used. Alternatively, a metal material such as gold, silver, platinum, magnesium, nickel, tungsten, chromium, molybdenum, iron, cobalt, copper, palladium, or titanium, or an alloy material containing the metal material can be used. Further alternatively, a nitride of the metal material (e.g., titanium nitride) or the like may be used. Note that in the case of using the metal material or the alloy material (or the nitride thereof), the thickness is preferably set small enough to be able to transmit light. A stacked-layer film of any of the above materials can be used as a conductive layer. For example, a stacked-layer film of indium tin oxide and an alloy of silver and magnesium, or the like is preferably used for increased conductivity. These materials can also be used for conductive layers such as a variety of wirings and electrodes that constitute a display panel, and conductive layers (conductive layers functioning as a pixel electrode or a common electrode) included in a display element.

As an insulating material that can be used for each insulating layer, for example, a resin such as an acrylic resin or an epoxy resin, and an inorganic insulating material such as silicon oxide, silicon oxynitride, silicon nitride oxide, silicon nitride, or aluminum oxide can be given.

Structure Example 3-2

Figure 13:
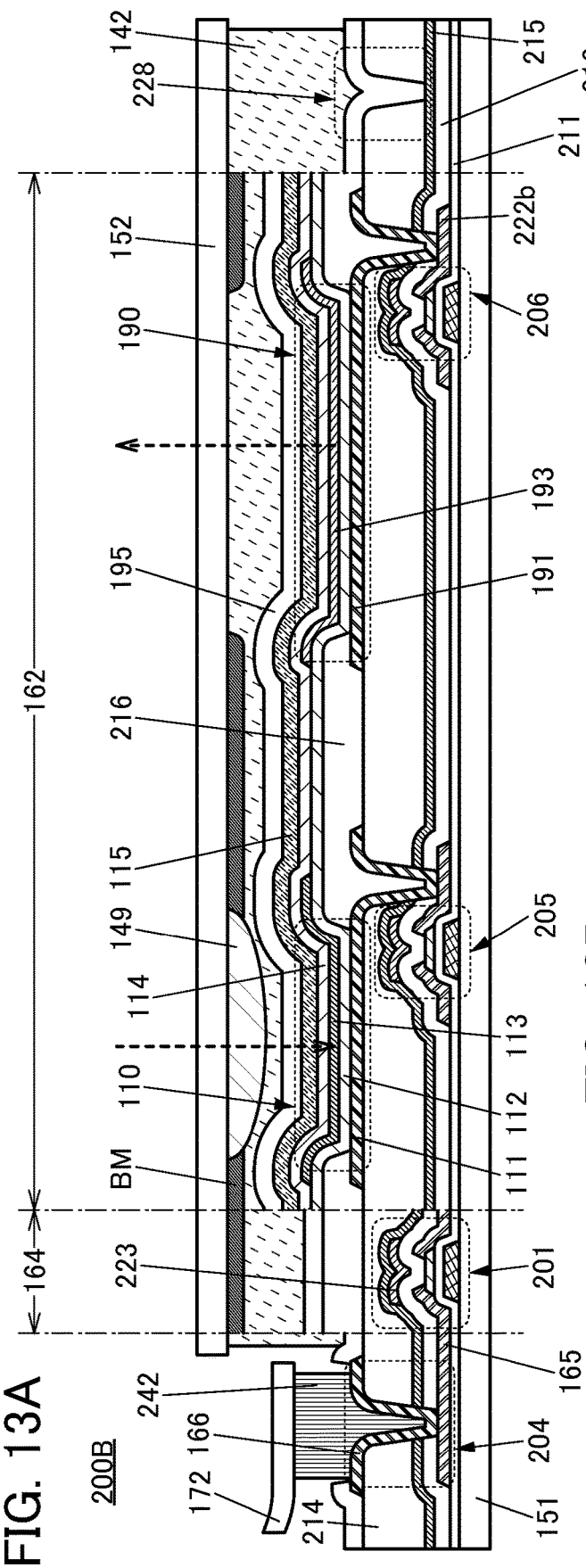
FIG. 13A and FIG. 13B are diagrams illustrating structure examples of a display device.

FIG. 13A illustrates a cross-sectional view of a display panel 200B. The display panel 200B is different from the display panel 200A mainly in that the lens 149 and the protective layer 195 are included.

Providing the protective layer 195 covering the light-receiving element 110 and the light-emitting element 190 can inhibit diffusion of impurities such as water into the light-receiving element 110 and the light-emitting element 190, so that the reliability of the light-receiving element 110 and the light-emitting element 190 can be increased.

In the region 228 in the vicinity of an end portion of the display panel 200B, the insulating layer 215 and the protective layer 195 are preferably in contact with each other through an opening in the insulating layer 214. In particular, the inorganic insulating film included in the insulating layer 215 and the inorganic insulating film included in the protective layer 195 are preferably in contact with each other. Thus, diffusion of impurities from the outside into the display portion 162 through the organic insulating film can be inhibited. Thus, the reliability of the display panel 200B can be increased.

FIG. 13B illustrates an example in which the protective layer 195 has a three-layer structure. In FIG. 13B, the protective layer 195 includes an inorganic insulating layer 195a over the common electrode 115, an organic insulating layer 195b over the inorganic insulating layer 195a, and an inorganic insulating layer 195c over the organic insulating layer 195b.

An end portion of the inorganic insulating layer 195a and an end portion of the inorganic insulating layer 195c extend beyond an end portion of the organic insulating layer 195b and are in contact with each other. The inorganic insulating layer 195a is in contact with the insulating layer 215 (inorganic insulating layer) through the opening in the insulating layer 214 (organic insulating layer). Accordingly, the light-receiving element 110 and the light-emitting element 190 can be surrounded by the insulating layer 215 and the protective layer 195, whereby the reliability of the light-receiving element 110 and the light-emitting element 190 can be increased.

As described above, the protective layer 195 may have a stacked-layer structure of an organic insulating film and an inorganic insulating film. In that case, an end portion of the inorganic insulating film preferably extends beyond an end portion of the organic insulating film.

The lens 149 is provided on a surface of the substrate 152 that faces the substrate 151. The lens 149 has a convex surface on the substrate 151 side. It is preferable that the light-receiving region of the light-receiving element 110 overlap with the lens 149 and not overlap with the light-emitting layer 193. Thus, the sensitivity and accuracy of a sensor using the light-receiving element 110 can be increased.

The refractive index of the lens 149 with respect to the wavelength of light received by the light-receiving element 110 is preferably greater than or equal to 1.3 and less than or equal to 2.5. The lens 149 can be formed using at least one of an inorganic material and an organic material. For example, a material containing a resin can be used for the lens 149. Moreover, a material containing at least one of an oxide and a sulfide can be used for the lens 149.

Specifically, a resin containing chlorine, bromine, or iodine, a resin containing a heavy metal atom, a resin having an aromatic ring, a resin containing sulfur, or the like can be used for the lens 149. Alternatively, a material containing a resin and nanoparticles of a material having a higher refractive index than the resin can be used for the lens 149. Titanium oxide, zirconium oxide, or the like can be used for the nanoparticles.

In addition, cerium oxide, hafnium oxide, lanthanum oxide, magnesium oxide, niobium oxide, tantalum oxide, titanium oxide, yttrium oxide, zinc oxide, an oxide containing indium and tin, an oxide containing indium, gallium, and zinc, and the like can be used for the lens 149. Alternatively, zinc sulfide or the like can be used for the lens 149.

In the display panel 200B, the protective layer 195 and the substrate 152 are bonded to each other with the adhesive layer 142. The adhesive layer 142 is provided to overlap with the light-receiving element 110 and the light-emitting element 190; that is, the display panel 200B employs a solid sealing structure.

Structure Example 3-3

Figure 14:
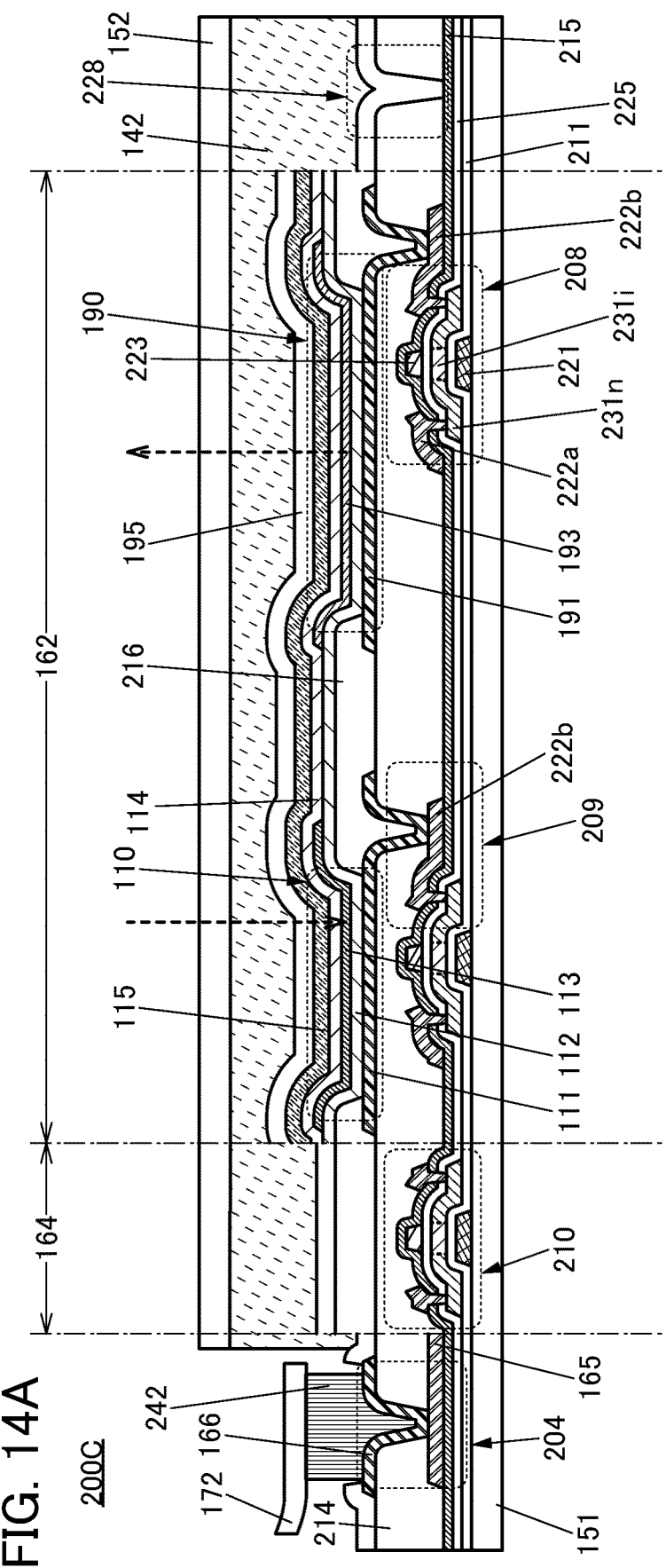
FIG. 14A and FIG. 14B are diagrams illustrating structure examples of display devices.

FIG. 14A illustrates a cross-sectional view of a display panel 200C. The display panel 200C is different from the display panel 200B mainly in the structure of the transistors and including neither the light-blocking layer BM nor the lens 149.

The display panel 200C includes a transistor 208, a transistor 209, and a transistor 210 over the substrate 151.

Each of the transistor 208, the transistor 209, and the transistor 210 includes the conductive layer 221 functioning as a gate, the insulating layer 211 functioning as a gate insulating layer, a semiconductor layer including a channel formation region 231$i$ and a pair of low-resistance regions 231$n$, the conductive layer 222$a$ connected to one of the pair of low-resistance regions 231$n$, the conductive layer 222$b$ connected to the other of the pair of low-resistance regions 231$n$, an insulating layer 225 functioning as a gate insulating layer, the conductive layer 223 functioning as a gate, and the insulating layer 215 covering the conductive layer 223. The insulating layer 211 is positioned between the conductive layer 221 and the channel formation region 231$i$. The insulating layer 225 is positioned between the conductive layer 223 and the channel formation region 231$i$.

The conductive layer 222$a$ and the conductive layer 222$b$ are connected to the corresponding low-resistance regions 231$n$ through openings provided in the insulating layer 225 and the insulating layer 215. One of the conductive layer 222$a$ and the conductive layer 222$b$ serves as a source, and the other serves as a drain.

The pixel electrode 191 of the light-emitting element 190 is electrically connected to one of the pair of low-resistance regions 231$n$ of the transistor 208 through the conductive layer 222$b$.

The pixel electrode 111 of the light-receiving element 110 is electrically connected to the other of the pair of low-resistance regions 231$n$ of the transistor 209 through the conductive layer 222$b$.

FIG. 14A illustrates an example in which the insulating layer 225 covers a top surface and a side surface of the semiconductor layer. Meanwhile, FIG. 14B illustrates an example in which the insulating layer 225 overlaps with the channel formation region 231$i$ of the semiconductor layer 231 and does not overlap with the low-resistance regions 231$n$ in a transistor 202. The structure illustrated in FIG. 14B can be obtained by processing the insulating layer 225 using the conductive layer 223 as a mask, for example. In FIG. 14B, the insulating layer 215 is provided to cover the insulating layer 225 and the conductive layer 223, and the conductive layer 222$a$ and the conductive layer 222$b$ are connected to the low-resistance regions 231$n$ through openings in the insulating layer 215. Furthermore, an insulating layer 218 covering the transistor may be provided.

Structure Example 3-4

Figure 15:
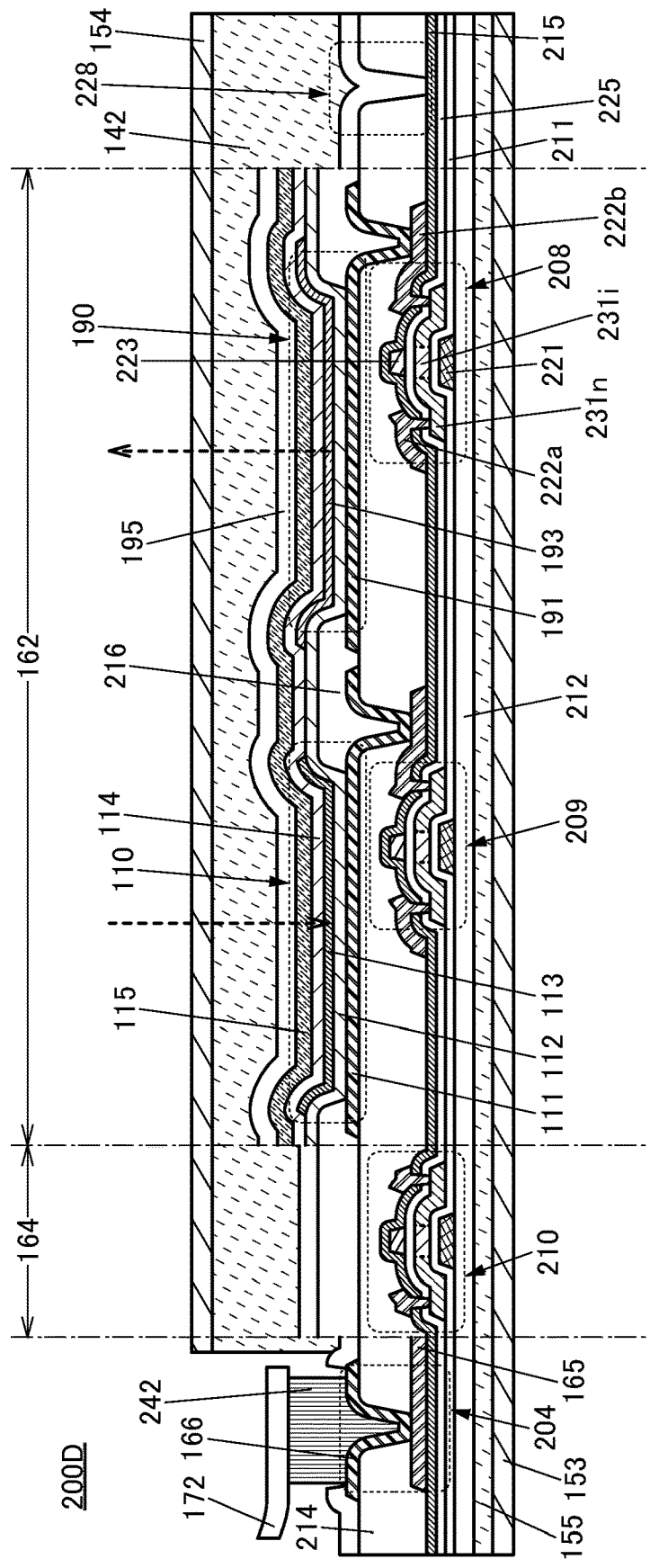
FIG. 15 is a diagram illustrating a structure example of a display device.

FIG. 15 illustrates a cross-sectional view of a display panel 200D. The display panel 200D is different from the display panel 200C mainly in the structure of the substrates.

The display panel 200D does not include the substrate 151 or the substrate 152 and includes the substrate 153, the substrate 154, the adhesive layer 155, and the insulating layer 212.

The substrate 153 and the insulating layer 212 are bonded to each other with the adhesive layer 155. The substrate 154 and the protective layer 195 are bonded to each other with the adhesive layer 142.

The display panel 200D has a structure obtained in such a manner that the insulating layer 212, the transistor 208, the transistor 209, the light-receiving element 110, the light-emitting element 190, and the like are formed over a formation substrate and then transferred onto the substrate 153. The substrate 153 and the substrate 154 preferably have flexibility. Accordingly, the flexibility of the display panel 200D can be increased.

The inorganic insulating film that can be used as the insulating layer 211, the insulating layer 213, and the insulating layer 215 can be used as the insulating layer 212. Alternatively, a stacked-layer film of an organic insulating film and an inorganic insulating film may be used as the insulating layer 212. In that case, a film on the transistor 209 side is preferably an inorganic insulating film.

The above is the description of the structure examples of the display panel.

[Metal Oxide]

A metal oxide that can be used for the semiconductor layer is described below.

Note that in this specification and the like, a metal oxide containing nitrogen is also collectively referred to as a metal oxide in some cases. A metal oxide containing nitrogen may be referred to as a metal oxynitride. For example, a metal oxide containing nitrogen, such as zinc oxynitride (ZnON), may be used for the semiconductor layer.

Note that in this specification and the like, CAAC (c-axis aligned crystal) or CAC (Cloud-Aligned Composite) may be stated. CAAC refers to an example of a crystal structure, and CAC refers to an example of a function or a material composition.

For example, a CAC (Cloud-Aligned Composite)-OS (Oxide Semiconductor) can be used for the semiconductor layer.

A CAC-OS or a CAC-metal oxide has a conducting function in part of the material and has an insulating function in another part of the material; as a whole, the CAC-OS or the CAC-metal oxide has a function of a semiconductor. In the case where the CAC-OS or the CAC-metal oxide is used in a semiconductor layer of a transistor, the conducting function is to allow electrons (or holes) serving as carriers to flow, and the insulating function is to not allow electrons serving as carriers to flow. By the complementary action of the conducting function and the insulating function, a switching function (On/Off function) can be given to the CAC-OS or the CAC-metal oxide. In the CAC-OS or the CAC-metal oxide, separation of the functions can maximize each function.

Furthermore, the CAC-OS or the CAC-metal oxide includes conductive regions and insulating regions. The conductive regions have the above-described conducting function, and the insulating regions have the above-described insulating function. Furthermore, in some cases, the conductive regions and the insulating regions in the material are separated at the nanoparticle level. Furthermore, in some cases, the conductive regions and the insulating regions are unevenly distributed in the material. Furthermore, in some cases, the conductive regions are observed to be coupled in a cloud-like manner with their boundaries blurred.

Furthermore, in the CAC-OS or the CAC-metal oxide, the conductive regions and the insulating regions each have a size greater than or equal to 0.5 nm and less than or equal to 10 nm, preferably greater than or equal to 0.5 nm and less than or equal to 3 nm, and are dispersed in the material, in some cases.

Furthermore, the CAC-OS or the CAC-metal oxide includes components having different band gaps. For example, the CAC-OS or the CAC-metal oxide includes a component having a wide gap due to the insulating region and a component having a narrow gap due to the conductive region. In the case of the structure, when carriers flow, carriers mainly flow in the component having a narrow gap. Furthermore, the component having a narrow gap complements the component having a wide gap, and carriers also flow in the component having a wide gap in conjunction with the component having a narrow gap. Therefore, in the case where the above-described CAC-OS or CAC-metal oxide is used in a channel formation region of a transistor, high current driving capability in an on state of the transistor, that is, a high on-state current and high field-effect mobility can be obtained.

In other words, the CAC-OS or the CAC-metal oxide can also be referred to as a matrix composite or a metal matrix composite.

Oxide semiconductors (metal oxides) are classified into a single crystal oxide semiconductor and a non-single-crystal oxide semiconductor. Examples of a non-single-crystal oxide semiconductor include a CAAC-OS (c-axis aligned crystalline oxide semiconductor), a polycrystalline oxide semiconductor, an nc-OS (nanocrystalline oxide semiconductor), an amorphous-like oxide semiconductor (a-like OS), and an amorphous oxide semiconductor.

The CAAC-OS has c-axis alignment, a plurality of nanocrystals are connected in the a-b plane direction, and its crystal structure has distortion. Note that the distortion refers to a portion where the direction of a lattice arrangement changes between a region with a regular lattice arrangement and another region with a regular lattice arrangement in a region where the plurality of nanocrystals are connected.

The nanocrystal is basically a hexagon but is not always a regular hexagon and is a non-regular hexagon in some cases. Furthermore, a pentagonal or heptagonal lattice arrangement, for example, is included in the distortion in some cases. Note that it is difficult to observe a clear crystal grain boundary (also referred to as grain boundary) even in the vicinity of distortion in the CAAC-OS. That is, formation of a crystal grain boundary is found to be inhibited by the distortion of a lattice arrangement. This is because the CAAC-OS can tolerate distortion owing to a low density of arrangement of oxygen atoms in the a-b plane direction, an interatomic bond length changed by substitution of a metal element, and the like.

The CAAC-OS tends to have a layered crystal structure (also referred to as a layered structure) in which a layer containing indium and oxygen (hereinafter, In layer) and a layer containing an element M, zinc, and oxygen (hereinafter, (M,Zn) layer) are stacked. Note that indium and the element M can be replaced with each other, and when the element M in the (M,Zn) layer is replaced with indium, the layer can also be referred to as an (In,M,Zn) layer. Furthermore, when indium in the In layer is replaced with the element M, the layer can be referred to as an (In,M) layer.

The CAAC-OS is a metal oxide with high crystallinity. On the other hand, a clear crystal grain boundary is difficult to observe in the CAAC-OS; thus, it can be said that a reduction in electron mobility due to the crystal grain boundary is unlikely to occur. Entry of impurities, formation of defects, or the like might decrease the crystallinity of a metal oxide; thus, it can be said that the CAAC-OS is a metal oxide that has small amounts of impurities and defects (e.g., oxygen vacancies (also referred to as $V_O$)). Thus, a metal oxide including a CAAC-OS is physically stable. Therefore, the metal oxide including a CAAC-OS is resistant to heat and has high reliability.

In the nc-OS, a microscopic region (e.g., a region with a size greater than or equal to 1 nm and less than or equal to 10 nm, in particular, a region with a size greater than or equal to 1 nm and less than or equal to 3 nm) has a periodic atomic arrangement. Furthermore, there is no regularity of crystal orientation between different nanocrystals in the nc-OS. Thus, the orientation in the whole film is not observed. Accordingly, the nc-OS cannot be distinguished from an a-like OS or an amorphous oxide semiconductor by some analysis methods.

Note that indium-gallium-zinc oxide (hereinafter, IGZO), which is a kind of metal oxide containing indium, gallium, and zinc, has a stable structure in some cases by being formed of the above-described nanocrystals. In particular, crystals of IGZO tend not to grow in the air and thus, a stable structure might be obtained when IGZO is formed of smaller crystals (e.g., the above-described nanocrystals) rather than larger crystals (here, crystals with a size of several millimeters or several centimeters).

An a-like OS is a metal oxide having a structure between those of the nc-OS and an amorphous oxide semiconductor. The a-like OS includes a void or a low-density region. That is, the a-like OS has low crystallinity as compared with the nc-OS and the CAAC-OS.

An oxide semiconductor (metal oxide) can have various structures that show different properties. Two or more of the amorphous oxide semiconductor, the polycrystalline oxide semiconductor, the a-like OS, the nc-OS, and the CAAC-OS may be included in an oxide semiconductor of one embodiment of the present invention.

A metal oxide film that functions as a semiconductor layer can be deposited using either or both of an inert gas and an oxygen gas. Note that there is no particular limitation on the flow rate ratio of oxygen (the partial pressure of oxygen) at the time of depositing the metal oxide film. However, to obtain a transistor having high field-effect mobility, the flow rate ratio of oxygen (the partial pressure of oxygen) at the time of depositing the metal oxide film is preferably higher than or equal to 0% and lower than or equal to 30%, further preferably higher than or equal to 5% and lower than or equal to 30%, still further preferably higher than or equal to 7% and lower than or equal to 15%.

The energy gap of the metal oxide is preferably 2 eV or more, further preferably 2.5 eV or more, still further preferably 3 eV or more. With use of a metal oxide having such a wide energy gap, the off-state current of the transistor can be reduced.

The substrate temperature during the deposition of the metal oxide film is preferably lower than or equal to 350° C., further preferably higher than or equal to room temperature and lower than or equal to 200° C., still further preferably higher than or equal to room temperature and lower than or equal to 130° C. The substrate temperature during the deposition of the metal oxide film is preferably room temperature because productivity can be increased.

The metal oxide film can be formed by a sputtering method. Alternatively, a PLD method, a PECVD method, a thermal CVD method, an ALD method, or a vacuum evaporation method, for example, may be used.

The above is the description of the metal oxide.

At least part of this embodiment can be implemented in combination with the other embodiments described in this specification as appropriate.

Embodiment 3

In this embodiment, a display panel that can be used in the system of one embodiment of the present invention is described with reference to FIG. 16A and FIG. 16B.

A display panel of one embodiment of the present invention includes first pixel circuits each including a light-receiving element and second pixel circuits each including a light-emitting element. The first pixel circuits and the second pixel circuits are arranged in a matrix.

Figure 16A:
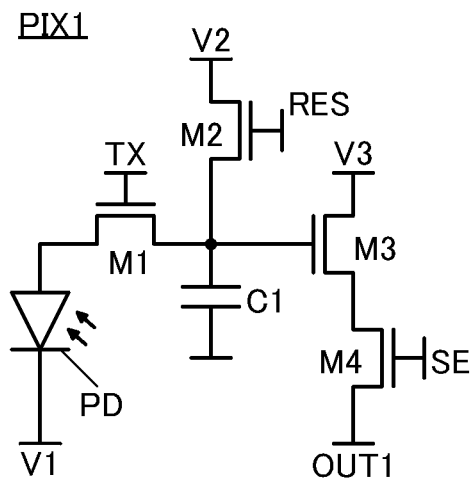
FIG. 16A and FIG. 16B are diagrams illustrating structure examples of pixel circuits.
Figure 16B:
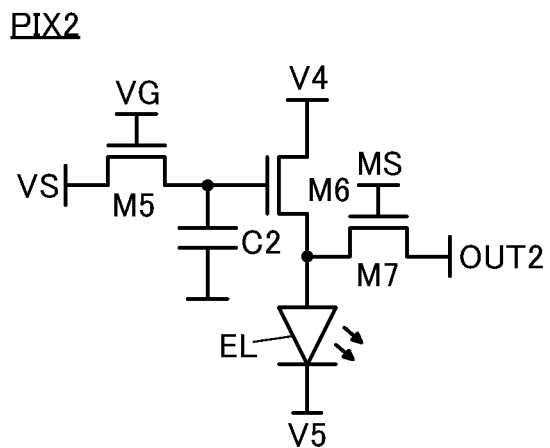

FIG. 16A illustrates an example of the first pixel circuit including a light-receiving element, and FIG. 16B illustrates an example of the second pixel circuit including a light-emitting element.

A pixel circuit PIX1 illustrated in FIG. 16A includes a light-receiving element PD, a transistor M1, a transistor M2, a transistor M3, a transistor M4, and a capacitor C1. Here, an example in which a photodiode is used as the light-receiving element PD is illustrated.

A cathode of the light-receiving element PD is electrically connected to a wiring V1, and an anode thereof is electrically connected to one of a source and a drain of the transistor M1. A gate of the transistor M1 is electrically connected to a wiring TX, and the other of the source and the drain thereof is electrically connected to one electrode of the capacitor C1, one of a source and a drain of the transistor M2, and a gate of the transistor M3. A gate of the transistor M2 is electrically connected to a wiring RES, and the other of the source and the drain thereof is electrically connected to a wiring V2. One of a source and a drain of the transistor M3 is electrically connected to a wiring V3, and the other of the source and the drain thereof is electrically connected to one of a source and a drain of the transistor M4. A gate of the transistor M4 is electrically connected to a wiring SE, and the other of the source and the drain thereof is electrically connected to a wiring OUT1.

A constant potential is supplied to the wiring V1, the wiring V2, and the wiring V3. When the light-receiving element PD is driven with a reverse bias, a potential lower than the potential of the wiring V1 is supplied to the wiring V2. The transistor M2 is controlled by a signal supplied to the wiring RES and has a function of resetting the potential of a node connected to the gate of the transistor M3 to a potential supplied to the wiring V2. The transistor M1 is controlled by a signal supplied to the wiring TX and has a function of controlling the timing at which the potential of the node changes, in accordance with a current flowing through the light-receiving element PD. The transistor M3 functions as an amplifier transistor for performing output in response to the potential of the node. The transistor M4 is controlled by a signal supplied to the wiring SE and functions as a selection transistor for reading an output corresponding to the potential of the node by an external circuit connected to the wiring OUT1.

A pixel circuit PIX2 illustrated in FIG. 16B includes a light-emitting element EL, a transistor M5, a transistor M6, a transistor M7, and a capacitor C2. Here, an example in which a light-emitting diode is used as the light-emitting element EL is illustrated. In particular, an organic EL element is preferably used as the light-emitting element EL.

A gate of the transistor M5 is electrically connected to a wiring VG, one of a source and a drain thereof is electrically connected to a wiring VS, and the other of the source and the drain thereof is electrically connected to one electrode of the capacitor C2 and a gate of the transistor M6. One of a source and a drain of the transistor M6 is electrically connected to a wiring V4, and the other thereof is electrically connected to an anode of the light-emitting element EL and one of a source and a drain of the transistor M7. A gate of the transistor M7 is electrically connected to a wiring MS, and the other of the source and the drain thereof is electrically connected to a wiring OUT2. A cathode of the light-emitting element EL is electrically connected to a wiring V5.

A constant potential is supplied to the wiring V4 and the wiring V5. In the light-emitting element EL, the anode side can have a high potential and the cathode side can have a lower potential than the anode side. The transistor M5 is controlled by a signal supplied to the wiring VG and functions as a selection transistor for controlling a selection state of the pixel circuit PIX2. The transistor M6 functions as a driving transistor that controls a current flowing through the light-emitting element EL, in accordance with a potential supplied to the gate. When the transistor M5 is in an on state, a potential supplied to the wiring VS is supplied to the gate of the transistor M6, and the emission luminance of the light-emitting element EL can be controlled in accordance with the potential. The transistor M7 is controlled by a signal supplied to the wiring MS and has a function of outputting a potential between the transistor M6 and the light-emitting element EL to the outside through the wiring OUT2.

Note that in the display panel of this embodiment, the light-emitting element may be made to emit light in a pulsed manner so as to display an image. A reduction in the driving time of the light-emitting element can reduce the power consumption of the display panel and suppress heat generation. An organic EL element is particularly preferable because of its favorable frequency characteristics. The frequency can be higher than or equal to 1 kHz and lower than or equal to 100 MHz, for example.

Here, a transistor using a metal oxide (an oxide semiconductor) in a semiconductor layer where a channel is formed is preferably used as the transistor M1, the transistor M2, the transistor M3, and the transistor M4 included in the pixel circuit PIX1 and the transistor M5, the transistor M6, and the transistor M7 included in the pixel circuit PIX2.

A transistor using a metal oxide having a wider band gap and a lower carrier density than silicon can achieve an extremely low off-state current. Thus, such a low off-state current enables retention of charge accumulated in a capacitor that is connected in series with the transistor for a long time. Therefore, it is particularly preferable to use a transistor using an oxide semiconductor as the transistor M1, the transistor M2, and the transistor M5 each of which is connected in series with the capacitor C1 or the capacitor C2. Moreover, the use of transistors using an oxide semiconductor as the other transistors can reduce the manufacturing cost.

Alternatively, transistors using silicon as a semiconductor where a channel is formed can be used as the transistor M1 to the transistor M7. In particular, the use of silicon with high crystallinity, such as single crystal silicon or polycrystalline silicon, is preferable because high field-effect mobility is achieved and higher-speed operation is possible.

Alternatively, a transistor using an oxide semiconductor may be used as one or more of the transistor M1 to the transistor M7, and transistors using silicon may be used as the other transistors.

Although the transistors are illustrated as n-channel transistors in FIG. 16A and FIG. 16B, p-channel transistors can alternatively be used.

The transistors included in the pixel circuit PIX1 and the transistors included in the pixel circuit PIX2 are preferably formed side by side over the same substrate. It is particularly preferable that the transistors included in the pixel circuit PIX1 and the transistors included in the pixel circuit PIX2 be periodically arranged in one region.

One or more layers including one or both of the transistor and the capacitor are preferably provided to overlap with the light-receiving element PD or the light-emitting element EL. Thus, the effective area of each pixel circuit can be reduced, and a high-resolution light-receiving portion or display portion can be achieved.

At least part of this embodiment can be implemented in combination with the other embodiments described in this specification as appropriate.

Embodiment 4

In this embodiment, electronic devices of embodiments of composite devices of embodiments of the present invention are described with reference to FIG. 17 to FIG. 19.

An electronic device in this embodiment includes the display device of one embodiment of the present invention. The display device has a function of detecting light, and thus can perform biometric authentication on the display portion and detect a touch or a near touch on the display portion. Unauthorized use of the electronic device of one embodiment of the present invention is difficult, that is, the electronic device has extremely high security level. Moreover, the electronic device can have improved functionality and convenience, for example.

Examples of the electronic devices include a digital camera, a digital video camera, a digital photo frame, a mobile phone, a portable game console, a portable information terminal, and an audio reproducing device, in addition to electronic devices with a relatively large screen, such as a television device, a desktop or laptop personal computer, a monitor of a computer or the like, digital signage, and a large game machine such as a pachinko machine.

The electronic device in this embodiment may include a sensor (a sensor having a function of measuring force, displacement, position, speed, acceleration, angular velocity, rotational frequency, distance, light, liquid, magnetism, temperature, a chemical substance, sound, time, hardness, electric field, current, voltage, electric power, radiation, flow rate, humidity, gradient, oscillation, a smell, or infrared rays).

The electronic device in this embodiment can have a variety of functions. For example, the electronic device can have a function of displaying a variety of data (a still image, a moving image, a text image, and the like) on the display portion, a touch panel function, a function of displaying a calendar, date, time, and the like, a function of executing a variety of software (programs), a wireless communication function, and a function of reading out a program or data stored in a recording medium.

Figure 17A:
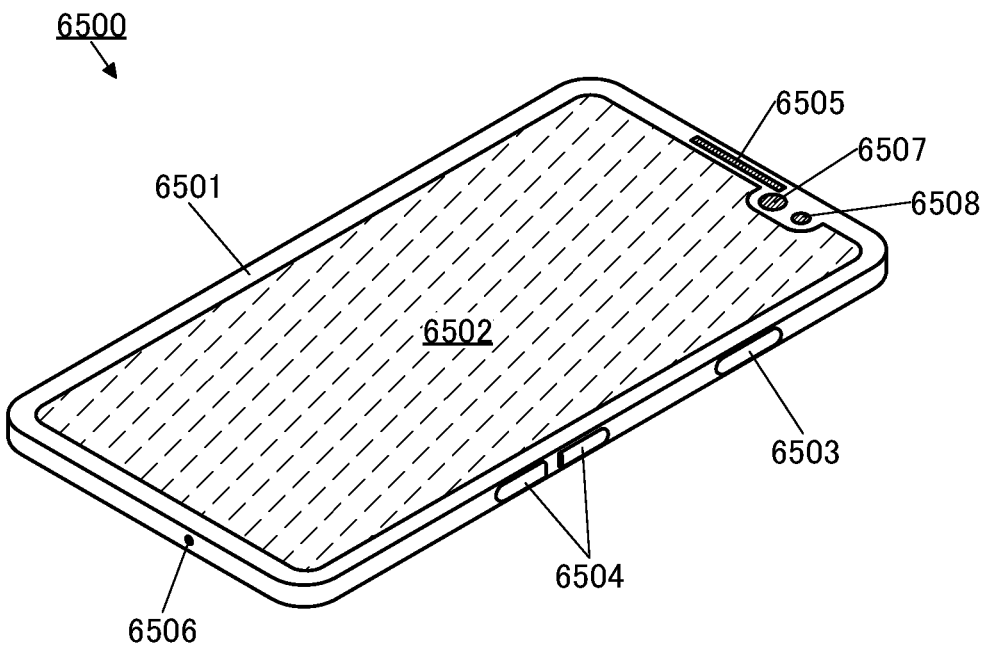
FIG. 17A and FIG. 17B are diagrams illustrating a structure example of an electronic device.

An electronic device 6500 illustrated in FIG. 17A is a portable information terminal that can be used as a smartphone.

The electronic device 6500 includes a housing 6501, a display portion 6502, a power button 6503, buttons 6504, a speaker 6505, a microphone 6506, a camera 6507, a light source 6508, and the like. The display portion 6502 has a touch panel function.

The display device of one embodiment of the present invention can be used in the display portion 6502.

Figure 17B:
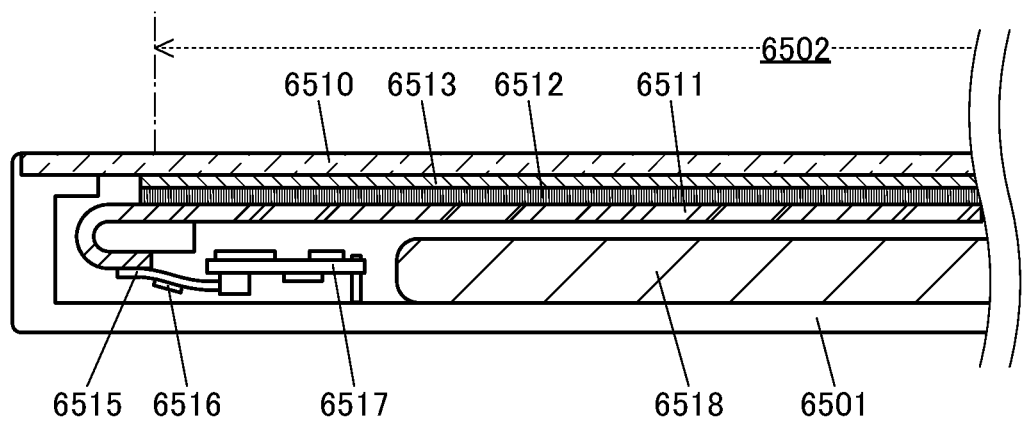

FIG. 17B is a schematic cross-sectional view including an end portion of the housing 6501 on the microphone 6506 side.

A protection member 6510 having a light-transmitting property is provided on the display surface side of the housing 6501, and a display panel 6511, an optical member 6512, a touch sensor panel 6513, a printed circuit board 6517, a battery 6518, and the like are provided in a space surrounded by the housing 6501 and the protection member 6510.

The display panel 6511, the optical member 6512, and the touch sensor panel 6513 are fixed to the protection member 6510 with an adhesive layer (not illustrated).

Part of the display panel 6511 is folded back in a region outside the display portion 6502, and an FPC 6515 is connected to the part that is folded back. An IC 6516 is mounted on the FPC 6515. The FPC 6515 is connected to a terminal provided on the printed circuit board 6517.

A flexible display of one embodiment of the present invention can be used as the display panel 6511. Thus, an extremely lightweight electronic device can be achieved. Since the display panel 6511 is extremely thin, the battery 6518 with high capacity can be mounted with the thickness of the electronic device controlled. An electronic device with a narrow frame can be achieved when part of the display panel 6511 is folded back so that the portion connected to the FPC 6515 is provided on the rear side of a pixel portion.

FIG. 18 illustrates an example of a television device. In a television device 7100, a display portion 7000 is incorporated in a housing 7101. Here, a structure in which the housing 7101 is supported by a stand 7103 is illustrated.

The display device of one embodiment of the present invention can be used in the display portion 7000.

Figure 18A:
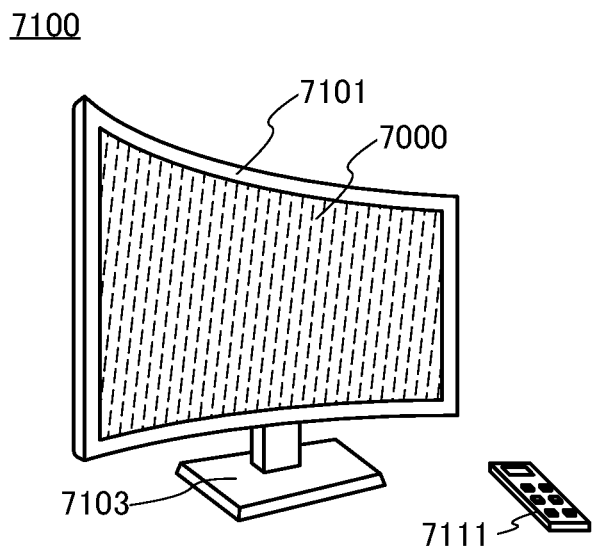
FIG. 18A to FIG. 18D are diagrams illustrating structure examples of electronic devices.

Operation of the television device 7100 illustrated in FIG. 18A can be performed with an operation switch provided in the housing 7101 or a separate remote controller 7111. Alternatively, the display portion 7000 may include a touch sensor, and the television device 7100 may be operated by a touch on the display portion 7000 with a finger or the like. The remote controller 7111 may be provided with a display portion for displaying data output from the remote controller 7111. With operation keys or a touch panel provided in the remote controller 7111, channels and volume can be operated and videos displayed on the display portion 7000 can be operated.

Note that the television device 7100 has a structure in which a receiver, a modem, and the like are provided. A general television broadcast can be received with the receiver. When the television device is connected to a communication network with or without wires via the modem, one-way (from a transmitter to a receiver) or two-way (between a transmitter and a receiver or between receivers, for example) data communication can be performed.

Figure 18B:
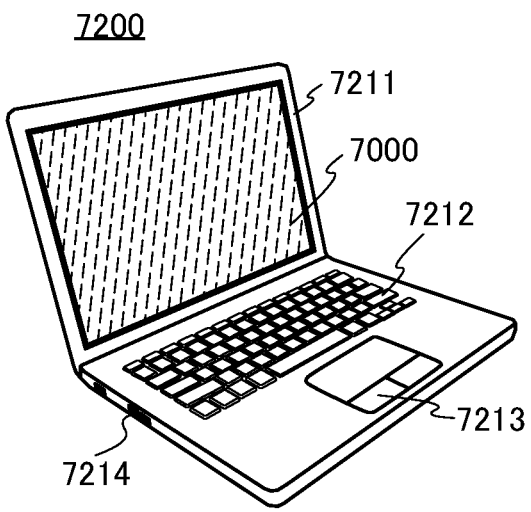

FIG. 18B illustrates an example of a laptop personal computer. A laptop personal computer 7200 includes a housing 7211, a keyboard 7212, a pointing device 7213, an external connection port 7214, and the like. In the housing 7211, the display portion 7000 is incorporated.

The display device of one embodiment of the present invention can be used in the display portion 7000.

Figure 18C:
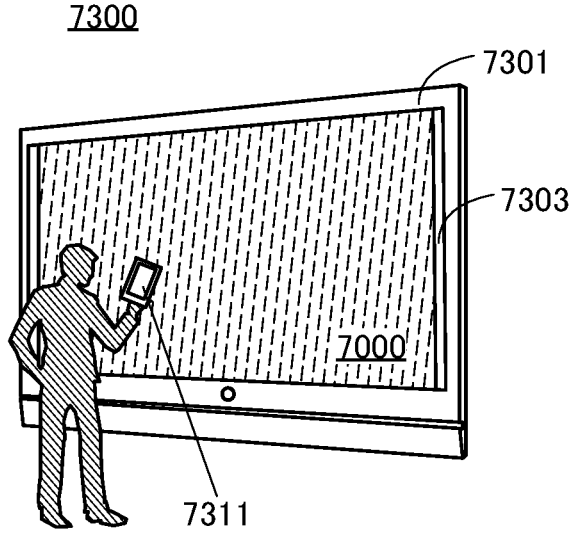
Figure 18D:
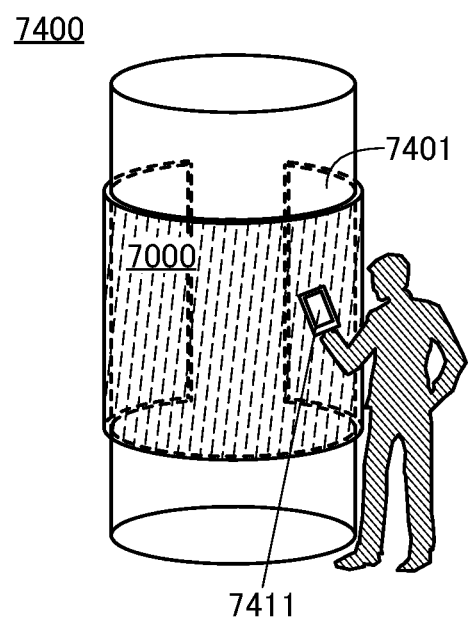

FIG. 18C and FIG. 18D illustrate examples of digital signage.

Digital signage 7300 illustrated in FIG. 18C includes a housing 7301, the display portion 7000, a speaker 7303, and the like. Furthermore, the digital signage can include an LED lamp, operation keys (including a power switch or an operation switch), a connection terminal, a variety of sensors, a microphone, and the like.

FIG. 18D is digital signage 7400 attached to a cylindrical pillar 7401. The digital signage 7400 includes the display portion 7000 provided along a curved surface of the pillar 7401.

The display device of one embodiment of the present invention can be used for the display portion 7000 in FIG. 18C and FIG. 18 and (D).

A larger area of the display portion 7000 can increase the amount of data that can be provided at a time. The larger display portion 7000 attracts more attention, so that the advertising effectiveness can be enhanced, for example.

The use of a touch panel in the display portion 7000 is preferable because in addition to display of an image or a moving image on the display portion 7000, intuitive operation by a user is possible. Moreover, for an application for providing information such as route information or traffic information, usability can be enhanced by intuitive operation.

As illustrated in FIG. 18C and FIG. 18D, the digital signage 7300 or the digital signage 7400 is preferably capable of working with an information terminal 7311 or an information terminal 7411 such as a user's smartphone through wireless communication. For example, information of an advertisement displayed on the display portion 7000 can be displayed on a screen of the information terminal 7311 or the information terminal 7411. By operation of the information terminal 7311 or the information terminal 7411, display on the display portion 7000 can be switched.

It is possible to make the digital signage 7300 or the digital signage 7400 execute a game with use of the screen of the information terminal 7311 or the information terminal 7411 as an operation means (controller). Thus, an unspecified number of users can join in and enjoy the game concurrently.

Electronic devices illustrated in FIG. 19A to FIG. 19F include a housing 9000, a display portion 9001, a speaker 9003, an operation key 9005 (including a power switch or an operation switch), a connection terminal 9006, a sensor 9007 (a sensor having a function of measuring force, displacement, position, speed, acceleration, angular velocity, rotational frequency, distance, light, liquid, magnetism, temperature, a chemical substance, sound, time, hardness, electric field, current, voltage, electric power, radiation, flow rate, humidity, gradient, oscillation, a smell, or infrared rays), a microphone 9008, and the like.

The electronic devices illustrated in FIG. 19A to FIG. 19F have a variety of functions. For example, the electronic devices can have a function of displaying a variety of information (a still image, a moving image, a text image, and the like) on the display portion, a touch panel function, a function of displaying a calendar, date, time, and the like, a function of controlling processing with use of a variety of software (programs), a wireless communication function, and a function of reading out and processing a program or data stored in a recording medium. Note that the functions of the electronic devices are not limited thereto, and the electronic devices can have a variety of functions. The electronic devices may include a plurality of display portions. The electronic devices may each include a camera or the like and have a function of taking a still image or a moving image and storing the taken image in a recording medium (an external recording medium or a recording medium incorporated in the camera), a function of displaying the taken image on the display portion, or the like.

The details of the electronic devices illustrated in FIG. 19A to FIG. 19F are described below.

Figure 19A:
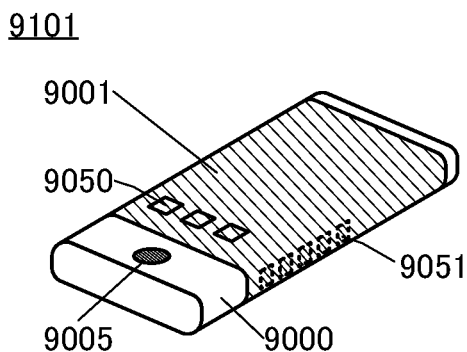
FIG. 19A to FIG. 19F are diagrams illustrating structure examples of electronic devices.

FIG. 19A is a perspective view illustrating a portable information terminal 9101. For example, the portable information terminal 9101 can be used as a smartphone. Note that the portable information terminal 9101 may be provided with the speaker 9003, the connection terminal 9006, the sensor 9007, or the like. The portable information terminal 9101 can display characters and image information on its plurality of surfaces. FIG. 19A illustrates an example where three icons 9050 are displayed. Information 9051 indicated by dashed rectangles can be displayed on another surface of the display portion 9001. Examples of the information 9051 include notification of reception of an e-mail, SNS, or an incoming call, the title and sender of an e-mail, SNS, or the like, the date, the time, remaining battery, and the reception strength of an antenna. Alternatively, the icon 9050 or the like may be displayed in the position where the information 9051 is displayed.

Figure 19B:
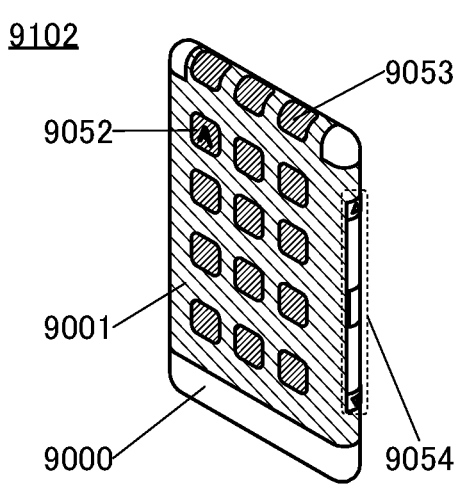

FIG. 19B is a perspective view illustrating a portable information terminal 9102. The portable information terminal 9102 has a function of displaying information on three or more surfaces of the display portion 9001. Here, an example in which information 9052, information 9053, and information 9054 are displayed on different surfaces is illustrated. For example, a user can check the information 9053 displayed in a position that can be observed from above the portable information terminal 9102, with the portable information terminal 9102 put in a breast pocket of his/her clothes. The user can see the display without taking out the portable information terminal 9102 from the pocket and decide whether to answer the call, for example.

Figure 19C:
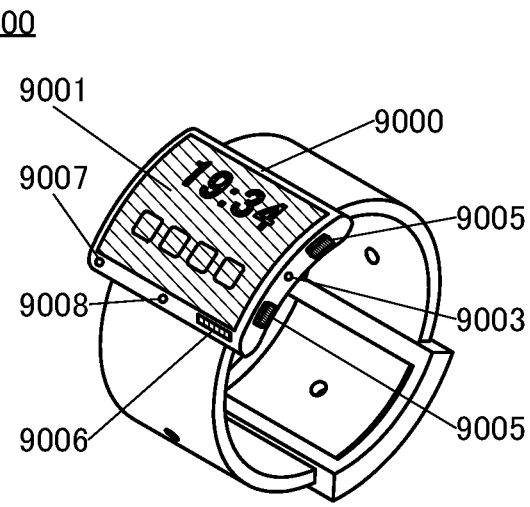

FIG. 19C is a perspective view illustrating a watch-type portable information terminal 9200. The display surface of the display portion 9001 is curved and provided, and display can be performed along the curved display surface. Mutual communication between the portable information terminal 9200 and, for example, a headset capable of wireless communication enables hands-free calling. With the connection terminal 9006, the portable information terminal 9200 can perform mutual data transmission with another information terminal and charging. Note that the charging operation may be performed by wireless power feeding.

Figure 19D:
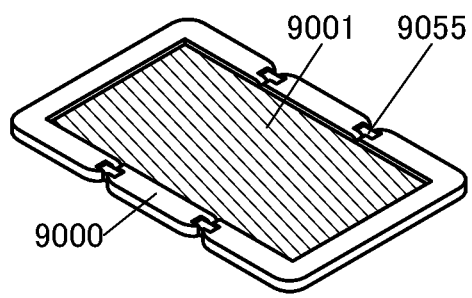
Figure 19E:
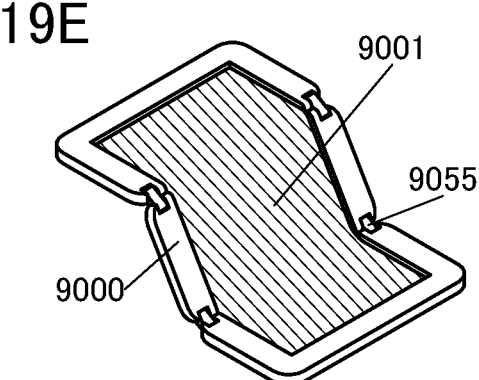
Figure 19F:
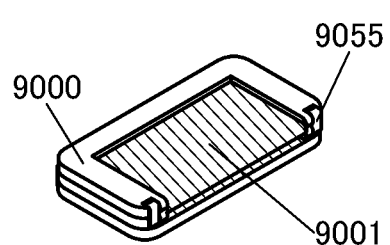

FIG. 19D, FIG. 19E, and FIG. 19F are perspective views illustrating a foldable portable information terminal 9201. FIG. 19D is a perspective view of an opened state of the portable information terminal 9201, FIG. 19F is a perspective view of a folded state thereof, and FIG. 19E is a perspective view of a state in the middle of change from one of FIG. 19D and FIG. 19F to the other. The portable information terminal 9201 is highly portable in the folded state and is highly browsable in the opened state because of a seamless large display region. The display portion 9001 of the portable information terminal 9201 is supported by three housings 9000 joined by hinges 9055. For example, the display portion 9001 can be bent with a radius of curvature greater than or equal to 0.1 mm and less than or equal to 150 mm.

At least part of this embodiment can be implemented in combination with the other embodiments described in this specification as appropriate.

REFERENCE NUMERALS

10, 10A: device, 11: control portion, 12: display portion, 13: authentication portion, 14: memory portion, 21: detection portion, 25, 25X: finger, 26, 26X, 27: fingerprint data, 30: electronic device, 31: display portion, 35: icon image, 36: information, 40, 40A, 40B: electronic device, 41, 41A, 41B, 41C: display portion, 42: input portion, 43: input key, 44: housing, 45: housing, 46: hinge portion

The invention claimed is:

1. A composite device comprising a control portion, a display portion, an authentication portion, and a memory portion,
    wherein the display portion is configured to display an image on a screen, to detect a touch on the screen, and to obtain first fingerprint data of a finger touching the screen,
    wherein the authentication portion is configured to execute user authentication processing,
    wherein the memory portion is configured to retain second fingerprint data, wherein the control portion is:
        configured to bring a system into an unlocked state when the authentication portion authenticates a user by employing at least one of a password, a pattern, and biological information of the user; and
        configured to compare the first fingerprint data and the second fingerprint data when the display portion detects a touch, and to bring the system into a locked state in the case where the first fingerprint data and the second fingerprint data do not match,
    wherein the display portion comprises:
        a light-emitting element and a light-receiving element over a substrate; and
        a light-blocking layer over the light-emitting element and the light-receiving element,
    wherein a first opening of the light-blocking layer overlaps with the light-emitting element, and
    wherein a second opening of the light-blocking layer overlaps with the light-receiving element.

2. The composite device according to claim 1,
    wherein the light-emitting element has a stacked-layer structure in which a first electrode, a light-emitting layer, and a common electrode are stacked,
    wherein the light-receiving element has a stacked-layer structure in which a second electrode, an active layer, and the common electrode are stacked,
    wherein the light-emitting layer and the active layer contain different organic compounds from each other, and
    wherein the common electrode covers the light-emitting layer and the active layer.

3. The composite device according to claim 1,
    wherein the light-emitting element has a stacked-layer structure in which a first electrode, a common layer, a light-emitting layer, and a common electrode are stacked,
    wherein the light-receiving element has a stacked-layer structure in which a second electrode, the common layer, an active layer, and the common electrode are stacked,
    wherein the light-emitting layer and the active layer contain different organic compounds from each other,
    wherein the common electrode is provided to cover the light-emitting layer and the active layer, and
    wherein the common layer covers the first electrode and the second electrode.

4. The composite device according to claim 1,
    wherein the light-emitting element is configured to emit visible light, and
    wherein the light-receiving element is configured to receive the visible light emitted from the light-emitting element.

5. The composite device according to claim 1,
    wherein the light-emitting element is configured to emit infrared light, and
    wherein the light-receiving element is configured to receive the infrared light emitted from the light-emitting element.

* * * * *